(12) United States Patent
Meseguer et al.

(10) Patent No.: US 7,193,092 B2
(45) Date of Patent: *Mar. 20, 2007

(54) CHIRAL DIPHOSPHORUS COMPOUNDS AND THEIR TRANSITION METAL COMPLEXES

(75) Inventors: Benjamin Meseguer, Tarragona (ES); Hans-Christian Militzer, Odenthal (DE); Sergio Castillon, Tarragona (ES); Carmen Claver, Tarragona (ES); Yolanda Diaz, Tarragona (ES); Mohamed Aghmiz, Tarragona (ES); Ester Guiu, Tarragona (ES); Ali Aghmiz, Tarragona (ES); Anna Masdeu, Tarragona (ES)

(73) Assignee: Lanxess Deutschland GmbH, Leverkusen (DE)

( * ) Notice: Subject to any disclaimer, the term of this patent is extended or adjusted under 35 U.S.C. 154(b) by 337 days.

This patent is subject to a terminal disclaimer.

(21) Appl. No.: 10/643,552

(22) Filed: Aug. 19, 2003

(65) Prior Publication Data

US 2005/0080047 A1    Apr. 14, 2005

(30) Foreign Application Priority Data

Aug. 21, 2002 (DE) ................ 102 38 115
Sep. 6, 2002 (DE) ................ 102 41 256

(51) Int. Cl.
*C07F 7/08*      (2006.01)
*C07F 7/18*      (2006.01)
*C07F 9/6553*    (2006.01)

(52) U.S. Cl. .............. 549/222; 549/216; 549/214; 549/206

(58) Field of Classification Search ........ 514/99; 549/429, 475, 206, 214, 216, 222
See application file for complete search history.

(56) References Cited

U.S. PATENT DOCUMENTS 5,175,335 A    12/1992    Casalnuovo et al. ........ 558/338
5,484,926 A    1/1996    Dressman et al. .......... 546/114
5,510,470 A *  4/1996    Casalnuovo et al. ....... 536/18.4
5,990,320 A    11/1999   Helmchen et al. .......... 885/218

FOREIGN PATENT DOCUMENTS

DE    91201      2/1897
EP    0639559    2/1995

OTHER PUBLICATIONS

T. V. RajanBabu, and Albert L. Casalnuovo; J. Am. Chem. Soc., (month unavailable) 1996, 188, pp. 6325-6326; "Role of Electronic Asymmetry in the Design of New Ligands: The Asymmetric Hydrocyanation Reaction".
T.V. RajanBabu et al; J. Org. Chem., (month unavailable) 1997, 62, pp. 6012-6028; "Carbohy-drate Phosphinites as Practical Ligands in Asymmetric Catalysis: Electronic Effects and Dependence of Backbone Chirality in Rh-Catalyzed Asymmetric Hydrogenations, Synthesis of R- or S-Amino Acids Using Natural Sugars as Ligand Precursors".
Journal of OrganicChemistry, V62, p. 6012; RajanBabu, Supplemental pp. 1-19.
A. Terfort Synthesis, Oct. 1992, 10, pp. 951-953; Synthesis and Application of (3R,4R)-3,4-Bis(diphenylphosphino)tetrahydrofuran as Ligand for Asymmetric Hydrogentation of Acrylic Acids.
W.R. Jackson and C. G. Lovel; Aust. J. Chem., (month unavailable) 1982, 35, pp. 2069-2075; "The Stereochemistry of Organometallic Compounds, XXIII* Synthesis of a Chiral Diphosphinite (diphin) and Evaluation of its Use as a Ligand for Asymmetric Catalysts".
A. Kless et al; Tetrahedron: Asymmetry, vol. 7, No. 1, pp. 33-36; (month unavailable) 1996 "Chiral Phosphinephosphites Having Axial and Central Chirality in Asymmetric Hydroformylations".
z. Lei, J.M. Min and L.H. Zhang; Tetrahedron: Asymmetry 11 (month unavailable) 2000, pp. 2899-2906; "Synthesis of 3-deoxy-3-nucleobase-2,5-anhydro-D-mannitol: a novel class of hydroxymethyl-branched isonucleosides".

* cited by examiner

*Primary Examiner*—Bernärd Dentz
(74) *Attorney, Agent, or Firm*—Michael A. Mitter

(57) ABSTRACT

The present invention relates to chiral diphosphorus compounds and their transition metal complexes, to a process for preparing chiral diphosphorus compounds and their transition metal complexes and also to their use in asymmetric syntheses.

7 Claims, No Drawings

CHIRAL DIPHOSPHORUS COMPOUNDS AND THEIR TRANSITION METAL COMPLEXES

BACKGROUND OF THE INVENTION

1. Field of the Invention

The present invention relates to chiral diphosphorus compounds and their transition metal complexes, to a process for preparing chiral diphosphorus compounds and their transition metal complexes and also to their use in asymmetric syntheses.

2. Brief Description of the Prior Art

Enantiomerically enriched chiral compounds are valuable starting substances for preparing agrochemicals and pharmaceuticals. Asymmetric catalysis for the synthesis of such enantiomerically enriched chiral compounds has gained great industrial significance.

The multitude of publications in the field of asymmetric synthesis shows clearly that transition metal complexes of diphosphorus compounds are particularly suitable as catalysts in asymmetric reactions. In particular, transition metal complexes of diphosphorus compounds have found use in industrial processes as catalysts in asymmetric hydrogenations of C=O, C=N and C=C bonds, hydrocyanations and hydroformylations.

For instance, U.S. Pat. No. 5,175,335; Rajan Babu, J. Am. Chem. Soc., 1996, 118, 6325–6326 and Rajan Babu, J. Org. Chem., 1997, 62, 6012–6028 disclose the use of enantiomerically enriched 1,6-substituted 3,4-(bisphosphinito)tetrahydrofurans and their transition metal complexes for asymmetric hydrocyanations and hydrogenations.

The use of the enantiomerically enriched 3,4-(bisphosphino) tetrahydrofurans and their transition metal complexes in asymmetric hydrogenations is also disclosed by EP-A 885 897 and A. Terfort, Synthesis, 1992, 10, 951–953. Enantiomerically enriched 3,4-(bisphosphito)tetrahydrofurans are described, for example, in W. R. Jackson, Aust. J. Chem., 1982, 35, 2069–2075 and, 3,4-(phosphinophosphito)tetrahydrofurans in A. Kless, Tetrahedron: Asymmetry, 1996, 7, 33–36.

The disadvantage of all of the enantiomerically enriched 3,4-(diphosphorus)-tetrahydrofurans mentioned is that steric and electronic variation of the central tetrahydrofuran framework, which is necessary for precise optimization and adaptation of the ligand and therefore of the catalyst for a given substrate, is only possible to a very limited extent and by numerous, complex synthetic steps. These disadvantages make industrial utilisation of such ligands and the catalysts preparable therefrom uneconomic.

There is therefore a need to develop a ligand system whose steric and electronic properties can be easily varied, and whose transition metal complexes as catalysts in asymmetric synthesis, in particular asymmetric hydrogenations, enable not only high enantioselectivity but also high conversion rates.

SUMMARY OF THE INVENTION

Diphosphorus compounds of the formula (I) have now been found

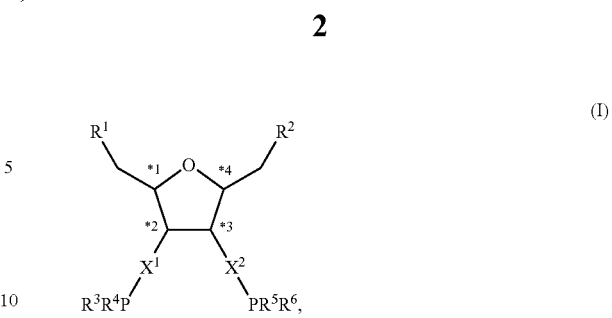

where
*1, *2, *3 and *4 are each independently a stereogenic carbon atom which is in the R- or S-configuration,
$X^1$ and $X^2$ are each independently absent or are oxygen and
$R^1$ and $R^2$ may each independently be: hydrogen, $C_1$–$C_{20}$-alkyl, $C_1$–$C_{20}$-fluoroalkyl, $C_2$–$C_{20}$-alkenyl, $C_4$–$C_{24}$-aryl, $C_5$–$C_{25}$-arylalkyl, $C_6$–$C_{26}$-arylalkenyl or $NR^7R^8$, $OR^8$, —($C_1$–$C_8$-alkyl)-$OR^8$, —($C_1$–$C_8$-alkyl)-$NR^7R^8$ or —$O_2CR^8$ where $R^7$ and $R^8$ are each independently $C_1$–$C_8$-alkyl, $C_5$–$C_{15}$-arylalkyl or $C_4$–$C_{14}$-aryl, or $R^7$ and $R^8$ together are a cyclic amino radical having a total of 4 to 20 carbon atoms,
or $R^1$ and $R^2$ are each independently radicals of the formula (II)

$$—R^9—SiR^{10}R^{11}R^{12} \qquad (II)$$

where
$R^9$ is absent, or is oxygen or methylene and
$R^{10}$, $R^{11}$ and $R^{12}$ are each independently $C_1$–$C_{12}$-alkyl, $C_5$–$C_{15}$-arylalkyl or $C_4$–$C_{14}$-aryl and
$R^3$, $R^4$, $R^5$ and $R^6$ are each independently $R^{13}$, $OR^{14}$ or $NR^{15}R^{16}$ where $R^{13}$, $R^{14}$, $R^{15}$ and $R^{16}$ are each independently $C_1$–$C_{12}$-alkyl, $C_5$–$C_{15}$-arylalkyl or $C_4$–$C_{14}$-aryl, or $NR^{15}R^{16}$ together is a cyclic amino radical having 4 to 20 carbon atoms, or $R^3$ and $R^4$ and/or $R^5$ and $R^6$ in each case together are —O—$R^{17}$—O— where $R^{17}$ is a radical selected from the group of $C_2$–$C_4$-alkylene, 1,2-phenylene, 1,3-phenylene, 1,2-cyclohexylene, 1,1'-ferrocenylene, 1,2-ferrocenylene, 2,2'-(1,1'-binaphthylene), 2,2'-(1,1')-biphenylene and 1,1'-(diphenyl-2,2'-methylene)-diyl, and the radicals mentioned may optionally be mono- or polysubstituted by radicals selected from the group of fluorine, chlorine, $C_1$–$C_8$-alkoxy and $C_1$–$C_8$-alkyl.

For the purposes of the invention, all radical definitions, parameters and illustrations mentioned hereinabove and hereinbelow, generally or in areas of preference, i.e. the particular areas and areas of preference, may be combined as desired.

DETAILED DESCRIPTION OF THE INVENTION

Alkyl, alkylene, alkoxy and alkenyl are in each case independently a straight-chain, cyclic, branched or unbranched alkyl, alkylene, alkoxy and alkenyl radical respectively. The same applies to the nonaromatic moiety of an arylalkyl radical.

$C_1$–$C_4$-Alkyl is, for example, methyl, ethyl, n-propyl, isopropyl, n-butyl, sec-butyl and tert-butyl, $C_1$–$C_8$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-ethyl-2-methylpropyl, n-heptyl and n-octyl, $C_1$–$C_{12}$-alkyl is further additionally, for example, adamantyl, the isomeric menthyls, n-nonyl, n-decyl and n-dodecyl, and $C_1$–$C_{20}$-alkyl is still further additionally, for example, n-hexadecyl and n-octadecyl.

$C_1$–$C_8$-Alkoxy is, for example, methoxy, ethoxy, n-propoxy, isopropoxy, n-butoxy, sec-butoxy and tert-butoxy, n-pentoxy, 1-methylbutoxy, 2-methylbutoxy, 3-methylbutoxy, neopentoxy, 1-ethylpropoxy, cyclohexoxy, cyclopentoxy, n-hexoxy and n-octoxy, and $C_1$–$C_{12}$-alkoxy is further additionally, for example, adamantoxy, the isomeric menthoxy radicals, n-decoxy and n-dodecoxy.

$C_2$–$C_{20}$-Alkenyl is, for example, vinyl, 1-propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 1-heptenyl, 1-octenyl or 2-octenyl.

Fluoroalkyl is in each case independently a straight-chain, cyclic, branched or unbranched alkyl radical which is singly, multiply or fully substituted by fluorine atoms.

$C_1$–$C_{20}$-fluoroalkyl is, for example, trifluoromethyl, 2,2,2-trifluoroethyl, pentafluoroethyl, nonafluorobutyl, perfluorooctyl, perfluorododecyl and perfluorohexadecyl.

Aryl is in each case independently a heteroaromatic radical having 5 to 18 framework carbon atoms of which no, one, two or three framework carbon atoms per cycle, but at least one framework carbon atom in the entire molecule, may be substituted by heteroatoms selected from the group of nitrogen, sulphur or oxygen, but is preferably a carbocyclic aromatic radical having 6 to 18 framework carbon atoms.

Examples of carbocyclic aromatic radicals having 6 to 18 framework carbon atoms are phenyl, naphtyl, phenanthrenyl, anthracenyl or fluorenyl, and heteroaromatic radicals having 5 to 18 framework carbon atoms on which no, one, two or three framework carbon atoms per cycle, but at least one framework carbon atom in the entire molecule, may be substituted by heteroatoms selected from the group of nitrogen, sulphur or oxygen are, for example, pyridinyl, oxazolyl, benzofuranyl, dibenzofuranyl or quinolinyl.

The carbocyclic aromatic radical or heteroaromatic radical may also be substituted by up to five identical or different substituents per cycle which are selected from the group of chlorine, fluorine, $C_1$–$C_{12}$-alkyl, $C_1$–$C_{12}$-fluoroalkyl, $C_1$–$C_{12}$-alkoxy, di($C_1$–$C_8$-alkyl)amino, COO($C_1$–$C_8$-alkyl), CON($C_1$–$C_8$-alkyl)$_2$, COO($C_1$–$C_8$-arylalkyl), COO($C_4$–$C_{14}$-aryl), CO($C_1$–$C_8$-alkyl), $C_5$–$C_{15}$-arylalkyl or tri($C_1$–$C_6$-alkyl)siloxyl.

The same applies to aryloxy radicals.

Arylalkyl is in each case independently a straight-chain, cyclic, branched or unbranched alkyl radical which may be singly, multiply or fully substituted by aryl radicals as defined above.

$C_5$–$C_{25}$-Arylalkyl is, for example, benzyl, diphenylbenzyl, triphenylbenzyl (trityl), 1-phenylethyl, 1-phenylpropyl, 2-phenylpropyl, 1-phenyl-1-methylethyl, 1-, 2-, 3- or 4-phenylbutyl, 1-phenyl-1-methylpropyl, 1-phenyl-2-methylpropyl, phenyl-1,1-dimethylethyl, 1-,2-,3-,4- or 5-phenylpentyl, phenyl-1-methylbutyl, phenyl-2-methylbutyl, phenyl-3-methylbutyl, phenyl-2,2-dimethylpropyl, phenyl-1-ethylpropyl, 1-naphthylmethyl, 1-naphthylethyl, naphthyl-1-methylethyl, naphthylbutyl, naphthyl-1-methylpropyl, naphthyl-2-methylpropyl, naphthyl-1,1-dimethylethyl, naphthylpentyl, naphthyl-1-methylbutyl, naphthyl-2-methylbutyl, naphthyl-3-methylbutyl, naphthyl-2,2-dimethylpropyl or naphthyl-1-ethylpropyl, and also their isomeric or stereoisomeric forms.

Arylalkenyl is in each case independently a straight-chain, cyclic, branched or unbranched alkenyl radical which may be singly, multiply or fully substituted by aryl radicals as defined above.

$C_6$–$C_{26}$-Arylalkenyl is, for example, 1-phenylvinyl or 2-phenylvinyl.

The preferred substitution patterns or compounds of the formula (I) are defined hereinbelow:

*1,*2,*3,*4 together define the following stereoisomers of the central substituted furan ring:
(1R,2R,3R,4R), (1R,2R,3R,4S), (1R,2R,3S,4S), (1R,2S,3R,4S), (1R,2S,3R,4S), (1R,2S,3S,4R), (1R,2R,3S,4R), (1S,2S,3R,4S), (1S,2S,3S,4S), (1S,2S,3S,4R), (1S,2S,3R,4R), (1S,2R,3R,4R), (1S,2R,3S,4R), (1S,2R,3R,4S), (1S,2S,3R,4S), (1R,2R,3S,4R), preferably (1R,2R,3R,4R), (1R,2R,3R,4S), (1R,2S,3S,4S), (1R,2S,3S,4R), (1R,2R,3S,4R), (1S,2S,3R,4S), (1S,2S,3S,4S), (1S,2S,3S,4R), (1S,2R,3R,4R), (1S,2R,3R,4S), (1S,2S,3R,4S), (1R,2R,3S,4R).

$R^1$ and $R^2$ are preferably each independently hydrogen, $C_1$–$C_4$-alkyl, $C_4$–$C_{14}$-aryl, O—$R^8$, $O_2$C—$R^8$, where $R^8$ is preferably $C_1$–$C_{12}$-alkyl, $C_5$–$C_{25}$-arylalkyl or $C_4$–$C_{14}$-aryl, or OSi$R^{10}R^{11}R^{12}$, where $R^{10}$, $R^{11}$, and $R^{12}$ are preferably each independently $C_1$–$C_{12}$-alkyl or $C_4$–$C_{14}$-aryl.

$R^1$ and $R^2$ are more preferably each independently hydrogen, tert-butoxy, trityloxy, tert-butyldimethylsilyloxy, tert-butyldiphenylsilyloxy, trimethylsilyloxy, triethylsilyloxy, triisopropylsilyloxy, neopentoxy or 1-adamantoxy.

For the purposes of the invention, preference is in each case given to those compounds of the formula (I) in which $R^1$ and $R^2$ are identical.

$R^3$, $R^4$, $R^5$ and $R^6$ are preferably each independently $R^{13}$, O$R^{14}$ or N$R^{15}R^{16}$ where $R^{13}$, $R^{14}$, $R^{15}$ and $R^{16}$ are each independently $C_1$–$C_{12}$-alkyl or $C_4$–$C_{14}$-aryl, or N$R^{15}R^{16}$ together is a cyclic amino radical having 4 to 12 carbon atoms, for example pyrrolidinyl or piperidinyl, or $R^3$ and $R^4$ and/or $R^5$ and $R^6$ together are each —O—$R^{17}$—O— where $R^{17}$ is ethylene, 1,2-phenylene, 1,3-phenylene, 1,2-cyclohexylene, 1,1'-ferrocenylene, 1,2-ferrocenylene, di- or tetra-$C_1$–$C_8$-alkyl-substituted 1,1'-(diphenyl-2,2'-methylene)-diyl, or 2,2'-(1,1'-binaphthylene) or 2,2'-(1,1')-biphenylene, and 2,2'-(1,1'-binaphthylene) or 2,2'-(1,1')-biphenylene is substituted at least in the 6,6'-position by radicals selected from the group of $C_1$–$C_8$-alkoxy and $C_1$–$C_8$-alkyl, and may also be substituted in the 5,5'-, 4,4'-, 3,3'- or 2,2'-position by radicals selected from the group of fluorine, chlorine, $C_1$–$C_8$-alkoxy and $C_1$–$C_8$-alkyl.

$R^3$, $R^4$, $R^5$ and $R^6$ are more preferably each independently $R^{13}$, O$R^{14}$ or N$R^{15}R^{16}$, where $R^{13}$ and $R^{14}$ are each independently methyl, ethyl, n-propyl, isopropyl, tert-butyl, cyclohexyl, phenyl, 2-($C_1$–$C_8$)-alkylphenyl such as o-tolyl, 3-($C_1$–$C_8$)-alkylphenyl such as m-tolyl, 4-($C_1$–$C_8$)-alkylphenyl such as p-tolyl, 2,6-di-($C_1$–$C_8$)-alkylphenyl such as 2,6-dimethylphenyl, 2,4-di-($C_1$–$C_8$)-alkylphenyl such as 2,4-dimethylphenyl, 3,5-di-($C_1$–$C_8$)-alkylphenyl such as 3,5-dimethylphenyl, 3,4,5-tri-($C_1$–$C_8$)-alkylphenyl such as mesityl and isityl, 2-($C_1$–$C_8$)-alkoxyphenyl such as o-anisyl and o-phenetyl, 3-($C_1$–$C_8$)-alkoxyphenyl such as m-anisyl and m-phenetyl, 4-($C_1$–$C_8$)-alkoxyphenyl such as p-anisyl and p-phenetyl, 2,4-di-($C_1$–$C_8$)-alkoxyphenyl such as 2,4-dimethoxyphenyl, 2,6-di-($C_1$–$C_8$)-alkoxyphenyl such as 2,6-dimethoxyphenyl, 3,5-di-(C₁–C₈)-alkoxyphenyl such as 3,5-dimethoxyphenyl, 3,4,5-tri-(C₁–C₈)-alkoxyphenyl such as 3,4,5-trimethoxyphenyl, 3,5-dialkyl-4-(C₁–C₈)-alkoxyphenyl such as 3,5-dimethyl-4-anisyl, 3,5-(C₁–C₈)-dialkyl-4-di-(C₁–C₈)-alkylaminophenyl, 3,5-dimethyl-4-dimethylamino-phenyl, 4-di-(C₁–C₈)-alkylaminophenyl such as 4-diethylaminophenyl and 4-dimethylaminophenyl, 3,5-bis-[(C₁–C₄)-fluoroalkyl]phenyl such as 3,5-bis-trifluoromethylphenyl, 2,4-bis-[(C₁–C₄)-fluoroalkyl]phenyl such as 2,4-bis-trifluoromethylphenyl, 4-[(C₁–C₄)-fluoroalkyl]phenyl such as 4-trifluoromethylphenyl and mono-, di-, tri-, tetra- or penta-fluorine- and/or -chlorine-substituted phenyl, fluorenyl or naphthyl, such as 4-fluorophenyl and 4-chlorophenyl, or $NR^{15}R^{16}$ as a whole is dimethylamino, diethylamino, pyrrolidino or diisopropylamino. $R^3$ and $R^4$ and/or $R^5$ and $R^6$, each in pairs, are also more preferably $O—R^{17}—O$ where $R^{17}$ is 1,1'-bis-(4,6-di-(C₁–C₈-alkyl)-phenyl)-2,2'-methylene)-diyl, in particular 1,1'-bis-(4-methyl-6-tert-butylphenyl-2,2'-methylene)-diyl and 1,1'-bis-(4-methyl-6-(1-methylcyclohexyl)-phenyl-2,2'-methylene)-diyl, or where $R^{17}$ is (R)-1,1'-biphenyl-2,2'-diyl, (S)-1,1'-biphenyl-2,2'-diyl, (R)-1,1'-binaphthyl-2,2'-diyl, (S)-1,1'-binaphthyl-2,2'-diyl, 1,1'-[bis-(4-methyl-6-tert-butylphenyl)-2,2'-methylene)]-diyl or 1,1'-[bis-(4-methyl-6-(1-methylcyclohexyl)-2,2-methylene)]-diyl.

For the purposes of the invention, preference is given in each case to those compounds of the formula (I) in which $R^3$ and $R^4$ and/or $R^5$ and $R^6$ in pairs are identical.

Particularly preferred compounds of the formula (I) are those of the formulae (Ia) to (Ii)

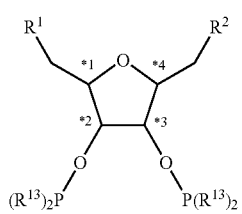
(Ia)

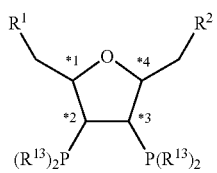
(Ib)

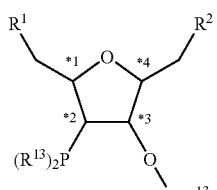
(Ic)

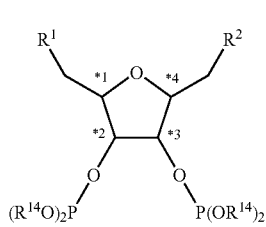
(Id)

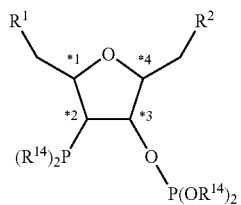
(Ie)

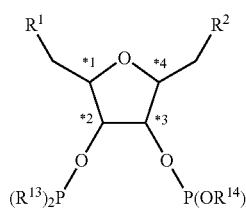
(If)

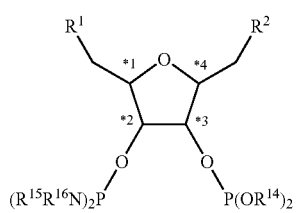
(Ig)

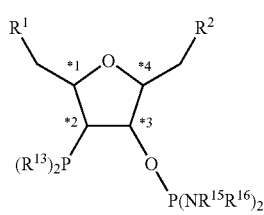
(Ih)

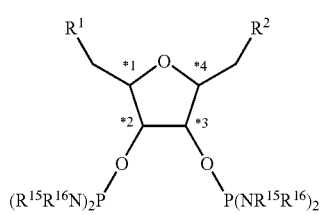
(Ij)

where *1, *2, *3, *4, $R^1$, $R^2$, $R^{13}$, $R^{15}$ and $R^{16}$ each have the definition and areas of preference specified under formula (I).

Compounds of the formula (I) include:
2,3-bis-O-(diphenylphosphino)-1,6-di-O-(triphenylmethyl)-2,5-anhydro-D-mannitol, 2,3-bis-O-(diphenylphosphino)-1,6-dideoxy-2,5-anhydro-D-mannitol, 2,3-bis-O-(diphenylphosphino)-1,6-di-O-(tert-butyldiphenylsilyl)-2,5-anhydro-D-mannitol, 2,3-bis-O-(diphenylphosphino)-1,6-di-O-(triphenylmethyl)-2,5-anhydro-L-iditol, 2,3-bis-O-(diphenylphosphino)-1,6-di-O-(tert-butyidiphenylsilyl)-2,5-anhydro-L-iditol, 2,3-bis-O-(diphenylphosphino)-1,6-dideoxy-2,5-anhydro-L-iditol, 2,3-bis-O-(di(4-methoxyphenyl)phosphino)-1,6-di-O-(tert-butyldiphenylsilyl)-2,5-anhydro-D-mannitol, 2,3-bis-O-(di((4-Trifluoromethyl)phenyl)phosphino)-1,6-di-O-(tert-butyldiphenylsilyl)-2,5-anhydro-D-mannitol, 2-O-(di(2,4-dimethylphenyl)phosphino)-3-O-(diphenylphosphino)-1,6-di-O-(tert-butyidiphenylsilyl)-2,5-anhydro-D-mannitol, 2-O-(di(2,4-dimethylphenyl)phosphino)-3-O-(4,8-ditert-butyl-2,10-dimethyl-12H-dibenzo[δ,γ][1,3,2]dioxaphosphocino)-1,6-di-O-(tert-butyldiphenylsilyl)-2,5-anhydro-D-mannitol and 2-O-(di(2,4-dimethylphenyl)phosphino)-3-O-(2,10-dimethyl-4,8-bis(1-methylcyclohexyl)-12H-dibenzo[δ,γ]-[1,3,2]dioxaphosphocino)-1,6-di-O-(tert-butyldiphenylsilyl)-2,5-anhydro-D-mannitol.

For the purposes of the invention, the term stereoisomerically enriched includes in particular stereoisomerically pure compounds or else mixtures of stereoisomeric compounds in which one stereoisomer is present in a larger relative proportion than the other stereoisomer or stereoisomers, preferably in a relative proportion of 50 to 100 mol %, more preferably 90 to 100 mol % and most preferably 98 to 100 mol %.

The compounds of the formula (I) and (Ia) to (Ii) can be prepared starting from the known 2,5-anhydrocyclopentoses of the formula (III).

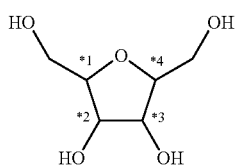

(III)

2,5-anhydrocyclopentoses of the formula (III) are, for example: 2,5-anhydro-D-mannitol, 2,5-anhydro-L-mannitol, 2,5-anhydro-L-iditol, 2,5-anhydro-D-iditol, 2,5-anhydro-L-glucitol, 2,5-anhydro-D-glucitol, 2,5-anhydro-altritol, 2,5-anhydro-D-altritol, 2,5-anhydro-galactitol, 2,5-anhydro-allitol.

Preferred compounds of the general formula (III) are:
2,5-anhydro-D-mannitol and 2,5-anhydro-L-iditol. For the purposes of the present invention, preference is given in particular to those compounds of the formula (I) which are obtainable starting from 2,5-anhydro-D-mannitol and 2,5-anhydro-L-iditol by the methods described hereinbelow.

The compounds of the formula (III) can be converted by reacting with compounds of the formula (IV)

$$R^{18}\text{-Hal} \quad (IV)$$

where
$R^{18}$ is $R^8$, $R^8CO$ or $OSiR^{10}R^{11}R^{12}$ and where $R^8$, $R^{10}$, $R^{11}$ and $R^{12}$ each have the definition and areas of preference specified under (I) or $R^{18}$ is $R^{19}$—$SO_2$— where $R^{19}$ is $C_1$–$C_{12}$-alkyl, $C_1$–$C_{12}$-fluoroalkyl, $C_5$–$C_{25}$-arylalkyl or $C_4$–$C_{24}$-aryl and
Hal is chlorine, bromine or iodine to compounds of the formula (V)

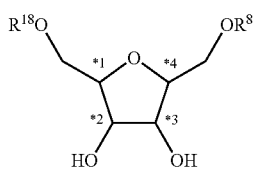

(V)

where $R^{18}$ is in each case independently as defined under formula (IV).

Compounds of the formula (V) where $R^{18}$ is $R^{19}SO_2$— can also be converted by reacting with amines of the formula (VI)

$$HNR^7R^8 \quad (VI)$$

where $R^7$ and $R^8$ each independently have the definitions and areas of preference specified under formula (I) to compounds of the formula (VII)

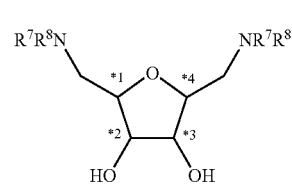

(VII)

where $R^7$ and $R^8$ are each independently as defined under formula (IV).

Compounds of the formula (V) in which $R^{18}$ is $R^{19}SO_2$— can also be converted by reacting with complex hydrides of the formula (VIII)

$$Met^1(AlR^{20}{}_nR^{21}{}_{(4-n)}) \quad (VIII)$$

where $Met^1$ is lithium, sodium or potassium, preferably lithium,
$R^{20}$ is hydrogen
n is 1, 2, 3 or 4, preferably 4 and
$R^{20}$ is $C_1$–$C_4$-alkyl,
or by reacting organolithium compounds of the formula (IX)

$$R^{20}\text{—Li} \quad (IX)$$

where $R^{20}$ is $C_1$–$C_{20}$-alkyl, $C_1$–$C_{20}$-fluoroalkyl, $C_2$–$C_{20}$-alkenyl, $C_4$–$C_{24}$-aryl, $C_5$–$C_{25}$-arylalkyl, $C_6$–$C_{26}$-arylalkenyl, —($C_1$–$C_8$-alkyl)-$OR^8$, —($C_1$–$C_8$-alkyl)-$NR^7R^8$ or protected (for example as a cyclic acetal)-($C^1$–$C_8$-alkyl)-CO—$R^8$ to compounds of the formula (X)

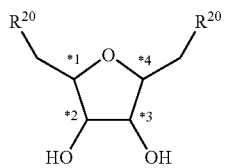

(X)

where $R^{20}$ is as defined under formulae (VIII) and (IX).

As a consequence of the acidity of the free 2- and 3-hydroxyl groups, it is advantageous to use an excess of the organolithium compounds or of the complex hydrides or to protect the 3,4-diol unit in a manner known per se by conversion, for example, to a cyclic acetal, and subsequently deprotecting it again.

The compounds of the formulae (V), (VII) and (X) together are encompassed by the compounds of the formula (XI), which can be used as intermediates for preparing the compounds of the formula (I) according to the invention.

In formula (XI)

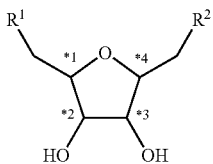

(XI)

$R^1$ and $R^2$ each have the same definition and areas of preference as described under formula (I).

The compounds of the formula (XI) can be used in a manner known in principle (see also Rajan Babu, J. Org. Chem., 1997, 62, 6012–6028), by reacting with compounds of the formula (XIIa)

(XIIa)

where $R^3$ and $R^4$ each have the same definition and areas or preference as specified under formula (I) and Y is chlorine, bromine, iodine, dimethylamino or diethylamino, preferably chlorine, to obtain the compounds of the formula (XIII)

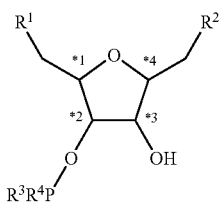

(XIII)

where $R^1$, $R^2$, $R^3$ and $R^4$ each have the same definition and areas of preference as described under formula (I).

The compounds of the formula (XIII) can also be reacted with compounds of the formula (XIIb)

(XIIb)

where $R^5$ and $R^6$ each have the same definitions and areas of preference as specified under formula (I) and Y has the same definition and areas of preference as specified under formula (XIIa)

to give compounds of the formula (XIV)

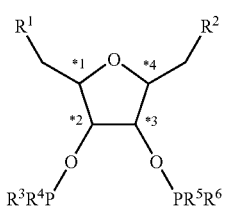

(XIV)

where $R^1$, $R^2$, $R^3$, $R^4$, $R^5$ and $R^6$ each have the same definitions and areas of preference as specified under formula (I).

When compound (XIIa) and (XIIb) are identical, the reaction can also be carried out in one step. Advantageously, the conversions of (XI) to (XIV), (XI) to (XIII) or (XIII) to (XIV) are carried out in the presence of a base, for example amines or aromatic nitrogen bases such as triethylamine, pyridine or 4-dimethylaminopyridine. Alternatively, the conversion can also be effected after at least partial deprotonation of the alcohol functions.

Examples of suitable solvents for the conversions are chlorinated alkanes such as methyl chloride, alkylic hydrocarbons, e.g. hexane, cyclohexane, aromatic hydrocarbons, e.g. toluene, pyridines, benzene, ketones, e.g. acetone, or carboxylic esters, e.g. ethyl acetate, or dialkyl ethers, e.g. THF or MTBE. The solvent used is preferably methylene chloride.

In the manner described, the compounds of the formulae (Ia), (Id), (If), (Ig) and (Ii) in particular with the above-specified definition and areas of preference are obtainable.

The compounds of the formulae (XIII) and (XIV) are likewise encompassed by the invention. The same definitions and areas of preference apply as specified under formula (I).

Compounds of the formula (XV)

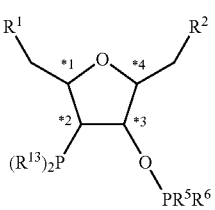

(XV)

where $R^1$, $R^2$, $R^5$, $R^6$ and $R^{13}$ each have the definitions and areas of preference specified under formula (I) can also be prepared by a process according to the invention by converting compounds of the formula (XVI)

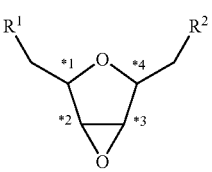

(XVI)

where $R^1$ and $R^2$ have the definition and areas of preference specified under formula (I), in the presence of compounds of the formula (XVII)

(XVII)

where $Met^2$ is lithium, sodium or potassium and $R^{13}$ has the definition and areas of preference specified under formula (I)

to compounds of the formula (XVIII)

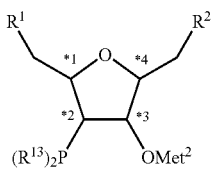
(XVIII)

where $R^1$, $R^2$, $Met^2$ and $R^{13}$ are each as defined above, and reacting the compounds of the formula (XVIII) with compounds of the formula (XIIb) as defined there to give compounds of the formula (XV).

Alternatively, the compounds of the formula (XVII) can be converted by acidifying to compounds of the formula (XIX)

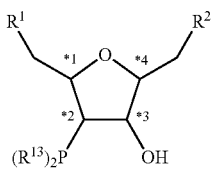
(XIX)

and then converted by reacting with compounds of the formula (XIIb) to compounds of the formula (XV). This reaction can be carried out as described for the preparation of the compounds of the formula (XIV).

The compounds of the formula (XV) include in particular the compounds of the formulae (Ic), (Ie), (If) and (Ih) preferred according to the invention.

The compounds of the formula (Ib)

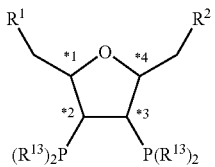
(Ib)

can be prepared, for example, in a manner known per se (see also Terfort, Synthesis, 1992, 951–953) by reacting compounds of the formula (XXa)

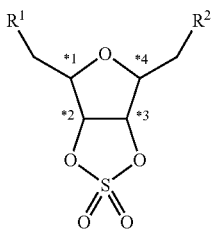
(XXa)

or compounds of the formula (XXb)

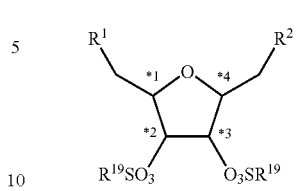
(XXb)

where $R^1$ and $R^2$ have the definition and areas of preference specified under formula (I) and $R^{19}$ has the definition and areas of preference specified under formula (VII) initially with phosphides of the formula (XVII), thus obtaining compounds of the formula (XXIa) or compounds of the formula (XXIb)

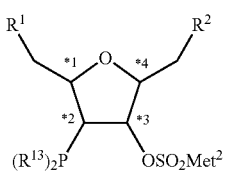
(XXIa)

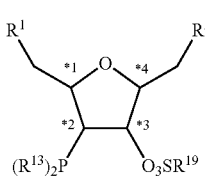
(XXIb)

and reacting the compounds of the formula (XXIa) or compounds of the formula (XXIb) with compounds of the formula (XVII) to give compounds of the formula (Ib).

When the radicals $P(R^{13})_2$ in formula (Ib) are identical, the conversion can also be effected in one step.

The compounds of the formulae (XXIa) and (XXIb) are likewise encompassed by the invention.

Some of the compounds of the formula (XXb) are known from the literature (see, for example, Tetrahedron: Asymmetry, 2000, 11, 2899 to 2906). Further compounds of the formulae (XXa) and (XXb) can be prepared in a similar manner to the literature. The compounds of the formula (XXb) are likewise encompassed by the invention as particularly suitable intermediate compounds for preparing compounds of the formula (I).

The invention also encompasses transition metal complexes which contain the compounds of the formula (I) according to the invention.

Transition metal complexes are preferably those of ruthenium, osmium, cobalt, rhodium, iridium, nickel, palladium, platinum and copper, preferably those of ruthenium, rhodium, iridium, nickel, palladium, platinum and copper.

The transition metal complexes according to the invention are suitable in particular as catalysts. The invention therefore also encompasses catalysts which contain the transition metal complexes according to the invention.

Useful catalysts are, for example, either isolated transition metal complexes or those transition metal complexes which are obtainable by reacting transition metal compounds and compounds of the formula (I).

Isolated transition metal complexes which contain the compounds of the formula (I) are preferably those in which the ratio of transition metal to compound of the formula (I) is 1:1.

Preference is given to the compounds according to the invention of the formula (XXIII)

[(I)L$^1{}_2$M] (XXIII)

where (I) is a compound of the formula (I) with the definition and areas of preference specified there and M is rhodium or iridium and L$^1$ is in each case a C$_2$–C$_{12}$-alkene, for example ethylene or cyclooctene, or a nitrile, for example acetonitrile or benzonitrile or benzyl nitrile, or L$^1{}_2$ together is a (C$_4$–C$_{12}$)-diene, for example bicyclo[2.1.1]hepta-2,5-diene (norbornadiene) or 1,5-cyclooctadiene.

Compounds of the formula (XXIII) include:

[Rh(cod)(2,3-bis-O-(diphenylphosphino)-1,6-di-O-(triphenylmethyl)-2,5-anhydro-D-mannitol)]BF$_4$, [Rh(cod)(2,3-bis-O-(diphenylphosphino)-1,6-di-O-(tert-butyidiphenylsilyl)-2,5-anhydro-D-mannitol)]BF$_4$, [Rh(cod)(2,3-bis-O-(diphenylphosphino)-1,6-dideoxy-2,5-anhydro-D-mannitol)]BF$_4$ and [Ir(cod)(2,3-bis-O-(diphenylphosphino)-1,6-di-O-(tert-butyidiphenylsilyl)-2,5-anhydro-D-mannitol)]BF$_4$.

Preferred transition metal complexes are those which are obtainable by reacting transition metal compounds and compounds of the formula (I).

Suitable transition metal compounds are, for example, those of the formula (XXIIa)

M(An$^1$)$_q$ (XXIIa)

where

M is rhodium, iridium, ruthenium, nickel, palladium, platinum or copper and

An$^1$ is chloride, bromide, acetate, nitrate, methanesulphonate, trifluoro-methanesulphonate or acetylacetonate and q is 3 for rhodium, iridium and ruthenium, is 2 for nickel, palladium and platinum, and is 1 for copper, or transition metal compounds of the formula (XXIIb), M(An$^2$)$_q$L$^1{}_2$ (XXIIb)

where

M is ruthenium, iridium, ruthenium, nickel, palladium, platinum or copper and

An$^2$ is chloride, bromide, acetate, methanesulphonate or trifluoro-methanesulphonate, tetrafluoroborate or hexafluorophosphate, perchlorate, hexafluoroantimonate, tetra(bis-3,5-trifluoromethylphenyl)-borate or tetraphenylborate and q is 1 for rhodium and iridium, is 2 for ruthenium, nickel, palladium and platinum, and is 1 for copper, L$^1$ is in each case a C$_2$–C$_{12}$-alkene, for example ethylene or cyclooctene, or a nitrile, for example acetonitrile, benzonitrile or benzyl nitrile, or L$^1{}_2$ together is a (C$_4$–C$_{12}$)-diene, for example bicyclo[2.1.1]hepta-2,5-diene (norbornadiene) or 1,5-cyclooctadiene.

or transition metal compounds of the formula (XXIIc),

[ML$^2$An$^1{}_2$]$_2$ (XXIIc)

where

M is ruthenium and

L$^2$ is an aryl radical, for example cymene, mesityl, phenyl or cyclooctadiene, norbornadiene or methylallyl or transition metal compounds of the formula (XXIId), Met$^3{}_q$[M(An$^3$)$_4$] (XXIId)

where

M is palladium, nickel, iridium or rhodium and

An$^3$ is chloride or bromide and

Met$^3$ is lithium, sodium, potassium, ammonium or organic ammonium and q is 3 for rhodium and iridium, and is 2 for nickel, palladium and platinum, or transition metal compounds of the formula (XXIIe),

[M(L$^3$)$_2$]An$^4$ (XXIIe)

where

M is iridium or rhodium and

L$^3$ is (C$_4$–C$_{12}$)-diene, for example bicyclo[2.1.1]hepta-2,5-diene (norbornadiene) or 1,5-cyclooctadiene and An$^4$ is a noncoordinating or weakly coordinating anion, for example methanesulphonate, trifluoromethanesulphonate, tetrafluoroborate, hexafluorophosphate, perchlorate, hexafluoroantimonate, tetra(bis-3,5-trifluoromethylphenyl)-borate or tetraphenylborate.

Also suitable as transition metal compounds are, for example, Ni(1,5-cyclooctadiene)$_2$, Pd$_2$(dibenzylideneacetone)$_3$, Pd[PPh$_3$]$_4$, cyclopentadienyl$_2$Ru, Rh(acac)(CO)$_2$, Ir(pyridine)$_2$(1,5-cyclooctadiene), Cu(phenyl)Br, Cu(phenyl)Cl, Cu(phenyl)I, Cu(PPh3)$_2$Br, [Cu(CH$_3$CN)$_4$]BF$_4$ and [Cu(CH$_3$CN)$_4$]PF$_6$ or multinuclear bridged complexes, for example [Rh(1,5-cyclooctadiene)Cl]$_2$, [Rh(1,5-cyclooctadiene)Br]2, [Rh(ethene)$_2$Cl]$_2$ or [Rh(cyclooctene)$_2$Cl]$_2$.

The transition metal compounds used are preferably: [Rh(cod)Cl]$_2$, [Rh(cod)Br]$_2$, [Rh(cod)$_2$]ClO$_4$, [Rh(cod)$_2$]BF$_4$, [Rh(cod)$_2$]PF$_4$, [Rh(cod)$_2$]ClO$_6$, [Rh(cod)$_2$]OTf, [Rh(cod)$_2$]BAr$_4$ (Ar=3,5-bistrifluoromethylphenyl), [Rh(cod)$_2$]SbF$_6$, RuCl$_2$(cod), [(cymene)RuCl$_2$]$_2$, [(benzene)-RuCl$_2$]$_2$, [(mesityl)RuCl$_2$]$_2$, [(cymene)RuBr$_2$]$_2$, [(cymene)RuI$_2$]$_2$, [(cymene)Ru(BF$_4$)$_2$]$_2$, [(cymene)Ru(PF$_6$)$_2$]$_2$, [(cymene)Ru(BAr$_4$)$_2$]$_2$ (Ar=3,5-bistrifluoromethylphenyl), [(cymene)Ru(SbF$_6$)$_2$]$_2$, [Ir(cod)Cl]$_2$, [Ir(cod)$_2$]PF$_6$, [Ir(cod)$_2$]ClO$_4$, [Ir(cod)$_2$]SbF$_6$, [Ir(cod)$_2$]BF$_4$, [Ir(cod)$_2$]OTf, [Ir(cod)$_2$]BAr$_4$ (Ar=3,5-bistrifluoromethylphenyl), RuCl$_3$, NiCl$_3$, RhCl$_3$, PdCl2, PdBr$_2$, Pd(OAc)$_2$, Pd$_2$(dibenzyleneacetone)$_3$, Pd(acetyl-acetonate)$_2$, CuOTf, CuI, CuCl, Cu(OTf)$_2$, CuBr, CuI, CuBr$_2$, CuCl$_2$, CuI$_2$, [Rh(nbd)Cl]$_2$, [Rh(nbd)Br]$_2$, [Rh(nbd)$_2$]ClO$_4$, [Rh(nbd)$_2$]BF$_4$, [Rh(nbd)$_2$]PF$_6$, [Rh(nbd)$_2$]OTf, [Rh(nbd)$_2$]BAr$_4$ (Ar=3,5-bistrifluoro-methylphenyl), [Rh(nbd)$_2$]SbF$_6$, RuCl$_2$(nbd), [Ir(nbd)$_2$]PF$_6$, [Ir(nbd)$_2$]ClO$_4$, [Ir(nbd)$_2$]SbF$_6$, [Ir(nbd)$_2$]BF$_4$, [Ir(nbd)$_2$]OTf, [Ir(nbd)$_2$]BAr$_4$ (Ar=3,5-bistrifluoromethylphenyl), Ir(pyridine)$_2$(nbd), [Ru(DMSO)$_4$Cl$_2$], [Ru(CH$_3$CN)$_4$Cl$_2$], [Ru(PhCN)$_4$Cl$_2$], [Ru(cod)Cl$_2$]$_n$, [Ru(cod)$_4$(methallyl)$_2$], [Ru(acetylacetonate)$_3$].

Still greater preference is given to [Rh(cod)Cl]$_2$, [Rh(cod)Br]$_2$, [Rh(cod)$_2$]ClO$_4$, [Rh(cod)$_2$]BF$_4$, [Rh(cod)$_2$]PF$_4$, [Rh(cod)$_2$]ClO$_6$, [Rh(cod)$_2$]OTf, [Rh(cod)$_2$]BAr$_4$ (Ar=3,5-bistrifluoromethylphenyl), [Rh(cod)$_2$]SbF$_6$, [Rh(nbd)Cl]$_2$, [Rh(nbd)Br]$_2$, [Rh(nbd)$_2$]ClO$_4$, [Rh(nbd)$_2$]BF$_4$, [Rh(nbd)$_2$]PF$_6$, [Rh(nbd)$_2$]OTf, [Rh(nbd)$_2$]BAr$_4$ (Ar=3,5-bistrifluoromethylphenyl), [Rh(nbd)$_2$]SbF$_6$, [Ir(cod)Cl]$_2$, [Ir(cod)$_2$]PF$_6$, [Ir(cod)$_2$]ClO$_4$, [Ir(cod)$_2$]SbF$_6$, [Ir(cod)$_2$]BF$_4$, [Ir(cod)$_2$]OTf, [Ir(cod)$_2$]BAr$_4$ (Ar=3,5-bistrifluoromethylphenyl).

The amount of the transition metal compounds used may, for example, be 25 to 200 mol %, based on the chiral diphosphorus compound of the general formula (I) used, preferably 50 to 150 mol %, very particularly preferably 75 to 125 mol % and even more preferably 100 to 115 mol %.

The catalysts which contain the transition metal complexes according to the invention are suitable in particular for use in a process for preparing stereoisomerically enriched, preferably enantiomerically enriched, compounds.

Preference is given to using the catalysts for asymmetric 1,4-additions, asymmetric hydroformylations, asymmetric hydrocyanations, asymmetric Heck reactions and asymmetric hydrogenations, more preferably for asymmetric hydrogenations.

Preferred asymmetric hydrogenations are, for example, hydrogenations of prochiral C═C bonds for example prochiral enamines, olefins, enol ethers, C═O bonds, for example prochiral ketones, and C═N bonds, for example prochiral imines. Particularly preferred asymmetric hydrogenations are hydrogenations of prochiral C═C bonds, for example prochiral enamines, olefins, and C═N bonds, for example prochiral imines.

The invention therefore also encompasses a process for preparing stereoisomerically enriched, preferably enantiomerically enriched, compounds by catalytic hydrogenation of olefins, enamines, enamides, imines or ketones, which is characterized in that the catalysts used are those which contain the transition metal complexes of compounds of the formula (I) as defined there.

The amount of the transition metal compound or of the transition metal complex used may, for example, be 0.001 to 5 mol %, based on the substrate used, preferably 0.001 to 0.5 mol %, very particularly preferably 0.001 to 0.1 mol % and even more preferably 0.001 to 0.008 mol %.

In a preferred embodiment, asymmetric hydrogenations can be carried out, for example, in such a manner that the catalyst is obtained for a transition metal compound and compound of the formula (I), optionally in a suitable solvent, the substrate is added and the reaction mixture is placed under hydrogen pressure at room temperature.

The metal compounds used for asymmetric hydrogenations are particularly preferably those of the general formula (XXIV)

[M(L³)₂]An⁴ (XXIV)

where M is rhodium or iridium, and L³ and An are as defined above, or dinuclear complexes, for example [Rh(1,5-cyclooctadiene)Cl]₂, [Rh(1,5-cyclooctadiene)Br]₂, [Rh(ethene)₂Cl]₂, [Rh(cyclooctene)₂Cl]₂.

Particularly preferred metal compounds for asymmetric hydrogenations are [Rh(cod)₂]OTf, [Rh(cod)₂]BF₄, [Rh(cod)₂]PF₆, [Rh(nbd)₂]PF₆, [Rh(nbd)₂]BF₄, and [Rh(norbornadiene)₂]OTf, [Ir(cod)₂]BF₄ and [Ir(cod)₂]PF₆].

In a particularly preferred embodiment, transition metal compound and compound of the formula (I) are dissolved in degassed solvent in a baked-out glass autoclave. The mixture is stirred for approx. 5 min and the substrate is subsequently added in degassed solvent. After setting a particular temperature, hydrogenation is effected under elevated H₂ pressure.

Suitable solvents for asymmetric catalysis are, for example, chlorinated alkanes such as methyl chloride, short-chain C₁–C₆-alcohols, e.g. methanol, isopropanol or ethanol, aromatic hydrocarbons, e.g. toluene or benzene, ketones, e.g. acetone, or carboxylic esters, e.g. ethyl acetate.

The asymmetric catalysis is advantageously carried out at a temperature of −20° C. to 200° C., preferably 0 to 100° C. and more preferably 20° to 70° C.

The hydrogen pressure may, for example, be 0.1 to 200 bar, preferably 0.5 to 100 bar and more preferably 1 to 70 bar.

The catalysts according to the invention are suitable in particular in a process for preparing stereoisomerically enriched, preferably enantiomerically enriched, active ingredients in pharmaceuticals and agrochemicals, or intermediates of these two classes.

The advantage of the present invention is that the ligands can be prepared in an efficient manner and their electronic and steric properties are variable to a high degree starting from readily available reactants. The ligands according to the invention and their transition metal complexes, especially in asymmetric hydrogenations of C═C bonds and imines, also exhibit turnover frequencies (TOFS) of over 1000/h, which are well above those of comparable systems.

The invention is further illustrated but is not intended to be limited by the following examples in which all parts and percentages are by weight unless otherwise specified.

EXAMPLES

Example 1

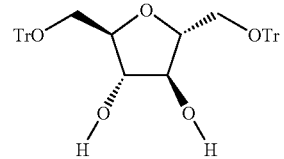

1,6-Di-O-(triphenylmethyl)-2,5-anhydro-D-mannitol (B1): a mixture of 2.35 g (14.33 mmol) of 2,5-anhydro-D-mannitol and 8.79 g (31.53 mmol) of triphenylmethyl chloride in 38 ml of pyridine was stirred at 100° C. for 12 hours. After cooling, the mixture was diluted with CH₂Cl₂, and washed with aq.HCl (0.78 mol/l), the organic phase was dried over Na₂SO₄ and the solvent was subsequently removed under reduced pressure. The crude product was purified by means of column chromatography (hexane/ethyl acetate 2:1). Yield: 5.57 g (60% of theory).

¹H NMR (400 MHz, CHCl₃) δ, 7.60–7.03 (m, 15H, Ph), 4.12 (m, 1H, H-2), 3.96 (m, 1H, H-3), 3.45 (dd, 1H, J₆,₂=3.9 Hz, J₆,₆'=10.2 Hz, H-6), 3.39 (sa, 1H, OH), 3.22 (dd, 1H, J₆',₂=4.2 Hz, J₆',₆=10.2 Hz, H-6'); ¹³C NMR (100.6 MHz) δ, 143.31.–127.02 (Ph), 87.31 (C(Ph)₃), 83.63 (C-2), 79.45 (C-3), 64.79 (C-6).

Example 2

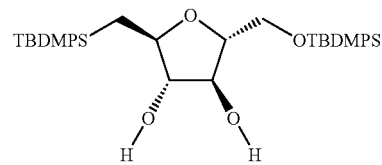

1,6-Di-O-(tert-butyldiphenylsilyl)-2,5-anhydro-D-mannitol (B2): 3 ml (11.66 mmol) of tert-butyldiphenylsilyl chloride (TBDMPSCl) were added dropwise at 0° C. to a solution of 0.87 g (5.3 mmol) of 2,5-anhydro-D-mannitol and 1.5 g (22.28 mmol) of imidazole in 12 ml of anhydrous DMF. The mixture was heated to room temperature and stirred for a further 25 hours, and the solvent was subsequently removed under reduced pressure. The mixture was diluted with $CH_2Cl_2$ and washed with water, the organic phase was dried over $Na_2SO_4$ and the solvent was subsequently removed under reduced pressure. The crude product was purified by means of column chromatography (hexane/ethyl acetate 4:1). Yield 1.36 g (40% of theory).

$^1$H NMR (400 MHz, $CDCl_3$) δ, 7.81–7.30 (m, 10H, Ph); 4.25 (m, 1H, H-3); 4.17 (m, 1H, H-2); 4.04 (d, 1H, OH); 3.86 (dd, 1H, $J_{6,2}$=3.7 Hz, $J_{6,6'}$=11.1 Hz, H-6); 3.75 (dd, 1H, $J_{6',2}$=3.2 Hz, $J_{6,6'}$=11.1 Hz, H-6'); 1.07 (s, 9H, C($CH_3$)$_3$); $^{13}$C NMR (100.6 MHz) δ, 136.10–126.99 (Ph), 87.09 (C-2), 79.71 (C-3), 65.52 (C-6), 26.73 (C($CH_3$)$_3$), 19.02 ( $C$($CH_3$)$_3$).

Example 3

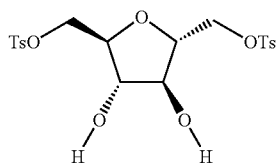

1,6-Di-O-(p-toluenesulphonyl)-2,5-anhydro-D-mannitol (B3): 5.33 g (27.945 mmol) of p-toluenesulphonyl chloride were added at 0° C. to a solution of 2.16 g (13.15 mmol) of 2,5-anhydro-D-mannitol in 88 ml of pyridine. The mixture was heated to room temperature and stirred for a further 24 hours. The reaction was hydrolysed using ice-water and extracted using $CH_2Cl_2$, and the combined organic phases were washed with 3N HCl and NaCl. After drying over $MgSO_4$, the solvent was subsequently removed under reduced pressure. The crude product was purified by means of column chromatography (hexane/ethyl acetate 1:2). Yield: 3.00 g (48% of theory).

$^1$H NMR (400 MHz, $CDCl_3$) δ, 7.82–7.31 (m, 4H, Ph); 4.2–3.9 (m, 4H, H-2, H-3, H-6, H-6'); 2.44 (s, 3H, $CH_3$); $^{13}$C NMR (100.6 MHz, $CDCl_3$) δ, 145.05–126.86 (Ph), 80.42 (C-2), 77.32 (C-3), 68.84 (C-6), 21.81 ($CH_3$).

Example 4

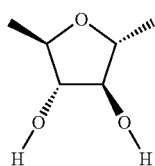

1,6-Dideoxy-2,5-anhydro-D-mannitol (B4): 0.86 g (22.66 mmol) of $LiAlH_4$ was added to a solution of 3.60 g (7.63 mmol) of B3 in 20 ml of anhydrous THF and stirred at reflux for 2 hours. After cooling, Arberlite® IR-120(plus) was added and stirring was continued until hydrogen evolution had ended. The mixture was filtered through Celite® and the solvent was subsequently removed under reduced pressure. The crude product was purified by means of column chromatography ($CH_2Cl_2$/MeOH=12:1). Yield: 0.84 g (84% of theory).

$^1$H NMR (400 MHz, $CDCl_3$) δ, 3.84 (m, 1H, H-2), 3.64 (m, 1H, H-3), 1.27 (d, 1H, $J_{6,2}$=6 Hz, H-6); $^{13}$C NMR (100.6 MHz; $CDCl_3$) δ, 84.18 (C-2), 79.29 (C-3), 19.61 (C-6).

Example 5

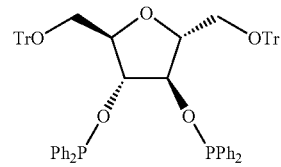

2,3-bis-O-(Diphenylphosphino)-1,6-di-O-(triphenylmethyl)-2,5-anhydro-D-mannitol (B5). 0.61 ml (4.4 mmol) of anhydrous $Et_3N$ was added to a solution of 0.63 g (1.0 mmol) of B1 in 5 ml of anhydrous, degassed $CH_2Cl_2$. At −15° C., a solution of 0.39 ml (2.2 mmol) of diphenylchlorophosphine in 3 ml of $CH_2Cl_2$ was slowly added dropwise. After stirring at −15° C. for 15 minutes, ethyl ether was added, the salts were filtered off through Celite® and the solvent was subsequently removed under reduced pressure. The crude product was purified by means of column chromatography under argon (hexane/ethyl acetate 15:1). Yield 0.51 g (51% of theory).

$[\alpha]_D$=+0.4 (c 1.04, $CHCl_3$); $^1$H NMR (400 MHz, $CHCl_3$) δ, 760.–7.02 (m, 25H, Ph), 4.62 (m, 1H, H-3), 4.29 (m, 1H, H-2), 3.198 (d, 2H, $J_{6,2}$=5.6 Hz, H-6, H-6'); $^{13}$C NMR (100.6 MHz) δ, 144.33–127.06 (Ph), 86.901 ($C$(Ph)$_3$), 86.14 (m, C-3), 83.51 (m, C-2), 64.25 (s, C-6); $^{31}$P NMR (161.974 MHz, $CDCl_3$) δ, 116.23 (s). Anal calcd for $C_{68}H_{58}O_5P_2$: C, 80.29; H, 5.74; found C, 79.99; H, 5.72.

Example 6

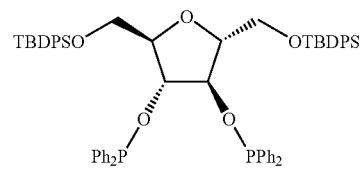

2,3-bis-O-(Diphenylphosphino)-1,6-di-O-(tert-butyl-diphenylsilyl)-2,5-anhydro-D-mannitol (B6): This product was prepared from B2 at −25° C. in a similar manner to Example 5. Yield: 0.816 g (50%), white oil.

$[\alpha]_D$=+9.9 (c 1.8, $CHCl_3$); $^1$H NMR (400 MHz, $CDCl_3$) δ, 7.81–7.02 (m, 20H, Ph), 4.88 (m, 1H, H-3), 4.18 (m, 1H, H-2), 3.76 (dd, 1H, JH-6), 3.63 (d, 1H, H-6'); 1.02 (s, 9H, C($CH_3$)$_3$); $^{13}$C NMR (100.6 MHz, $CDCl_3$) δ, 144.02–126.10 (Ph), 86.14 (m, C-3), 83.51 (m, C-2), 64.25 (s, C-6), 26.79 (C($CH_3$)$_3$), 19.26 ($C$($CH_3$)$_3$); $^{31}$P NMR (161.974 MHz, $CDCl_3$) δ, 116.23 (s).

Anal calcd for $C_{62}H_{66}O_5P_2Si_2$: C, 73.78; H, 6.59; found C, 73.65; H, 6.57.

Example 7

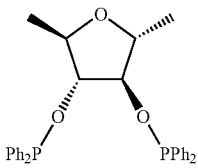

2,3-bis-O-(Diphenylphosphino)-1,6-dideoxy-2,5-anhydro-D-mannitol (B7): This product was prepared from B4 in a similar manner to Example 5. Yield: 58% of theory.

$[\alpha]_D$=−20.4 (c 1.04, $CHCl_3$); $^1H$ NMR (400 MHz, $CDCl_3$) δ, 7.60–7.02 (m, 10H, Ph), 4.26 (m, 1H, H-3), 4.12 (m, 1H, H-2), 1.21 (d, 3H, $J_{6,2}$=6.4 Hz, H-6); $^{13}C$ NMR (100.6 MHz, $CDCl_3$) δ, 142.12–127.08 (Ph), 90.74 (m, C-2), 78.35 (m, C-3), 19.15 (s, C-6); $^{31}P$ NMR (161.974 MHz, $CDCl_3$) δ, 114.39 (s). Anal calcd for $C_{30}H_{30}O_3P_2$: C, 71.99; H, 6.04; found C, 72.22; H, 6.06.

Example 8

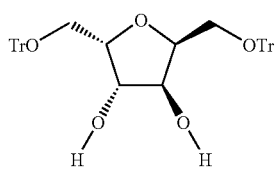

1,6-di-O(Triphenylmethyl)-2,5-anhydro-L-iditol (B8): This product was prepared starting from 2,5-anhydro-L-iditol in a similar manner to Example 1.

$^1H$ NMR (400 MHz, $CHCl_3$) δ, 7.60–7.02 (m, 15H, Ph), 4.42 (m, 1H, H-2), 4.25 (m, 1H, H-3), 3.48 (dd, 1H, $J_{6,2}$=5.4 Hz, $J_{6,6'}$=9.6 Hz, H-6), 3.40 (dd, 1H, $J_{6',2}$=3.8 Hz, $J_{6',6}$=9.8 Hz, H-6'); 3.24 (sa, 1H, OH), $^{13}C$ NMR (100.6 MHz) δ, 143.20.–127.01 (Ph), 87.20 ($\underline{C}(Ph)_3$), 78.78 (C-2), 78.65 (C-3), 62.78 (C-6).

Example 9

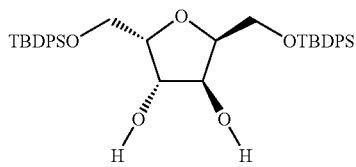

1,6-di-O-(tert-Butyldiphenylsilyl)-2,5-anhydro-L-iditol (B9): This product was prepared starting from 2,5-anhydro-L-iditol in a similar manner to Example 2.

$^1H$ NMR (400 MHz, $CDCl_3$) δ, 7.81–7.32 (m, 10H, Ph); 4.26 (m, 1H, H-2); 4.38 (m, 1H, H-3); 4.07 (d, 1H, $J_{6,2}$=4.4 Hz, $J_{6,6'}$=10.8 Hz, H-6), 4.05 (d, 1H, $J_{6',2}$=3.2 Hz, $J_{6',6}$=10.8 Hz, H-6'); 3.99 (d, 1H, OH); 1.06 (s, 9H, C($C\underline{H}_3)_3$); $^{13}C$ NMR (100.6 MHz) δ, 135.52–127.6 (Ph), 79.74 (C-2), 78.95 (C-3), 63.74 (C-6), 26.79 (C($\underline{C}H_3)_3$), 19.19 ($\underline{C}(CH_3)_3$).

Example 10

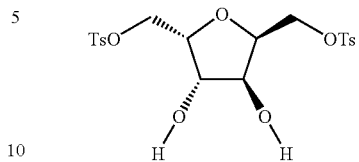

1,6-di-O-(p-Toluenesulphonyl)-2,5-anhydro-L-iditol (B10)

This product was prepared starting from 2,5-anhydro-L-iditol in a similar manner to Example 3.

$^1H$ NMR (400 MHz, $CDCl_3$) δ, 7.83–7.21 (m, 4H, Ph); 4.42–3.91 (m, 5H, H-2, H-3, H-6, H-6', OH); 2.44 (s, 3H, $CH_3$); $^{13}C$ NMR (100.6 MHz, $CDCl_3$) δ, 145.11–127.83 (Ph), 77.83 (C-2), 76.54 (C-3), 67.22 (C-6), 21.82 ($CH_3$).

Example 11

1,6-Dideoxy-2,5-anhydro-L-iditol (B11)

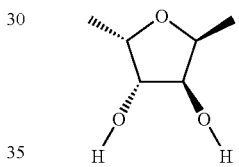

This product was prepared starting from B10 in a similar manner to Example 4.

$^1H$ NMR (400 MHz, $CDCl_3$) δ, 4.22 (m, 1H, H-2), 3.90 (m, 1H, H-3), 1.18 (d, 1H, $J_{6,2}$=6.6 Hz, H-6); $^{13}C$ NMR (100.6 MHz; $CDCl_3$) δ, 79.66 (C-2), 77.30 (C-3), 14.68 (C-6).

Example 12

2,3-bis-O-(Diphenylphosphino)-1,6-di-O-(triphenylmethyl)-2,5-anhydro-L-iditol (B12)

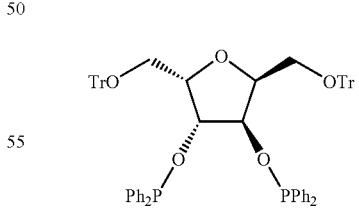

This product was prepared starting from B8 in a similar manner to Example 5.

$^1H$ NMR (400 MHz, $CHCl_3$) δ, 750.–7.51 (m, 25H, Ph), 4.30 (m, 1H, H-2), 4.37 (m, 1H, H-3), 3.48 (dd, 1H, $J_{6,2}$=9.4 Hz, $J_{6,6'}$=9.4 Hz, H-6); 3.18 (dd, 1H, $J_{6',2}$=5.8 Hz, $J_{6',6}$=9.4 Hz, H-6') $^{13}C$ NMR (100.6 MHz) δ, 143.91–126.62 (Ph), 86.77 ($\underline{C}(Ph)_3$), 82.64 (m, C-3), 79.654 (d, C-2), 62.82 (s, C-6); $^{31}P$ NMR (161.974 MHz, $CDCl_3$) δ, 114.12 (s).

Example 13

2,3-bis-O-(Diphenylphosphino)-1,6-di-O-(tert-butyl-diphenylsilyl)-2,5-anhydro-L-iditol (B13)

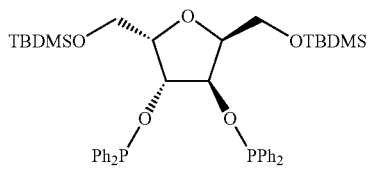

This product was prepared starting from B9 in a similar manner to Example 5.

$^1$H NMR (400 MHz, CDCl$_3$) δ, 7.81–7.09 (m, 20H, Ph), 4.51 (m, 1H, H-3), 4.21 (m, 1H, H-2), 3.85 (dd, 1H, J$_{6,2}$=7.4 Hz, J$_{6,6'}$=10.0 Hz H-6), 3.72 (dd, 1H, J$_{6',2}$=5.8 Hz, J$_{6',6}$=10.0 Hz, H-6'), 0.94 (s, 9H, C(CH$_3$)$_3$); $^{13}$C NMR (100.6 MHz, CDCl$_3$) δ, 135.51–127.43 (Ph), 83.09 (m, C-3), 80.68 (d, C-2), 61.73 (s, C-6), 26.92 (C(CH$_3$)$_3$), 19.25 (C(CH$_3$)$_3$); $^{31}$P NMR (161.974 MHz, CDCl$_3$) δ, 115.74 (s).

Example 14

2,3-bis-O-(Diphenylphosphino)-1,6-dideoxy-2,5-anhydro-L-iditol (B14)

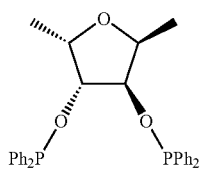

This product was prepared starting from B11 in a similar manner to Example 5.

$^1$H NMR (400 MHz, CDCl$_3$) δ, 7.63–7.21 (m, 10H, Ph), 4.32 (m, 1H, H-2), 4.23 (m, 1H, H-3), 1.20 (d, 3H, J$_{6,2}$=6.4 Hz, H-6); $^{13}$C NMR (100.6 MHz, CDCl$_3$) δ, 142.05–127.99 (Ph), 84.97 (m, C-3), 76.02 (m, C-2), 15.18 (s, C-6); $^{31}$P NMR (161.974 MHz, CDCl$_3$) δ, 114.05 (s).

Example 15

[Rh(cod)(B5)]BF$_4$ (B15): 0.030 g (0.073 mmol) of [Rh(cod)$_2$]BF$_4$ was dissolved in 10 ml of CH$_2$Cl$_2$. A solution of 0.090 g (0.088 mmol) of compound B5 in 3 ml CH$_2$Cl$_2$ was added to the solution and the resulting solution was stirred for 30 min. The solvent was removed under reduced pressure and the crude product was washed with anhydrous hexane and with ethyl ether. Yield: 0.042 g (43% of theory).

[α]$_D$=+119.41 (c 1.05, CHCl$_3$); $^1$H NMR (400 MHz, CDCl$_3$) δ, 7.60–7.02 (m, 25H, Ph), 5.36 (m, 1H, H-3), 4.70 (m, 2H, CH(cod)); 4.47 (m, 1H, H-2), 3.58 (dd, 1H, J$_{6,2}$=2.8 Hz, J$_{6,6'}$=10.8 Hz, H-6), 3.18 (dd, 1H, J$_{6,2}$=3.2 Hz, J$_{6',6}$=10.8 Hz, H-6'); 2.42–2.00 (m, 4H, CH$_2$(cod)); $^{13}$C NMR (100.6 MHz) δ, 144.10–126.05 (Ph, cod), 87.00 (C(Ph)$_3$), 82.67 (s, C-3), 82.45 (m, C-2), 63.33 (s, C-6); $^{31}$P NMR (161.974 MHz, CDCl$_3$) δ, 122.61 (d, J$_{P,Rh}$=166.18 Hz)).

Example 16

[Rh(cod)(B6)]BF$_4$ (B16): This complex was prepared from B6 in a similar manner to Example 15. Yield: 68% of theory.

[α]$_D$=(c, CHCl$_3$); $^1$H NMR (400 MHz, CDCl$_3$) δ, 7.82–7.21 (m, 20H, Ph), 5.24 (m, 1H, H-3), 4.77 (m, 1H, CH(cod)); 4.67 (m, 1H, CH(cod)); 4.19 (m, 1H, H-2), 3.85 (dd, 1H, J$_{6,2}$=2.4 Hz, J$_{6,6'}$=11.6 Hz, H-6), 3.69 (dd, 1H, J$_{6',2}$=3.2 Hz, J$_{6,6'}$=11.6 Hz, H-6'); 2.41–2.20 (m, 4H, CH$_2$(cod)); 1.04 (s, 9H, C(CH$_3$)$_3$); $^{13}$C NMR (100.6 MHz, CDCl$_3$) δ, 134.10–126.07 (Ph, cod), 82.53 (m, C-2), 81.23 (s, C-3), 63.13 (s, C-6), 26.95 (C(CH$_3$)$_3$), 19.44 (C(CH$_3$)$_3$); $^{31}$P NMR (161.974 MHz, CDCl$_3$) δ, 125.136 (d, J$_{P,Rh}$=167.97 Hz).

Example 17

[Rh(cod)(B7)]BF$_4$ (B17): This complex was prepared starting from B7 in a similar manner to Example 15. Yield: 55% of theory.

$^1$H NMR (400 MHz, CDCl$_3$) δ, 7.81–7.42 (m, 10H, Ph), 4.73 (m, 1H, CH(cod)); 4.64 (m, 1H, CH(cod)); 4.39 (m, 1H, H-3), 3.91 (m, 1H, H-2),); 2.61–2.20 (m, 4H, CH$_2$(cod)); 1.13 (d, 3H, J$_{6,2}$=6.0 Hz, H-6); $^{13}$C NMR (100.6 MHz, CDCl$_3$) δ, 133.15–128.03 (Ph, cod), 85.76 (s, C-3), 75.68 (m, C-2), 18.64 (s, C-6); $^{31}$P NMR (161.974 MHz, CDCl$_3$) δ, 127.39 (d, J$_{P,Rh}$=169.42 Hz).

Example 18

[Ir(cod)(B6)]BF$_4$ (B18): A solution of 102 mg (0.1 mmol) of compound B6 in 2 ml of CH$_2$Cl$_2$ was added dropwise to a solution cooled to −80° C. of 40 mg (0.08 mmol) of [Ir(cod)$_2$]BF$_4$ in 2 ml CH$_2$Cl$_2$. The resulting yellow solution was heated to 0° C. and stirred for a further 15 minutes. The solvent was partly removed under reduced pressure, 30 ml of ethyl ether were added and the solids were filtered off and washed. Yield: 98.6 mg, 86% of theory.

$^1$H NMR (400 MHz, CDCl$_3$) δ, 7.44–7.24 (m, 50H, CH arom), 5.35 (m, 2H, CH), 5.17 (m, 1H, CH); 4.52 (m, 2H, CH); 4.41 (m, 4H, CH$_2$); 3.60 (dd, J=2.6 Hz, J=10.4 Hz, 2H, CH$_2$), 3.21 (dd, J=2.6 Hz, J=10.4 Hz, 2H, CH$_2$), 2.42 (m, 2H, cod), 2.21 (m, 2H,), 2.06 (m, 2H), 1.67 (m, 2H). $^{13}$C NMR (100.6 MHz) δ, 143.6 (C arom.), 132.4 (s, arom); 32.0 (s, arom); 131.7 (t, arom.), 131.2 (t, arom.), 129.1 (m, arom.), 128.7 (m, arom.), 128.68 (s, CH arom.), 128.1 (s, CH arom.), 127.4 (s, CH arom), 95.5 (s, CH), 83.3 (s, CH), 87.2 (s, C), 83.1 (s, CH), 82.4 (s, CH), 63.7 (CH$_2$), 31.3 (s, CH$_2$), 31.1 (s, CH$_2$). $^{31}$P NMR (161.9 MHz, CDCl$_3$) δ, 104.6.

Examples 19–41

Rhodium-catalysed Hydrogenation of Enamides and Methyl Itaconate

In a glass autoclave, 6.1 mg (0.015 mmol) of [Rh(cod)$_2$]BF$_4$ were dissolved in 15 ml of degassed CH$_2$Cl$_2$, 0.016 mmol of ligand and 1 mmol of substrate were added under nitrogen and hydrogenation was effected at room temperature and 1 atm of hydrogen pressure. Conversion and ee were determined by gas chromatography.

Ligands:

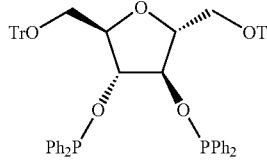
B5

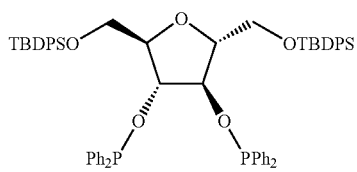
B6

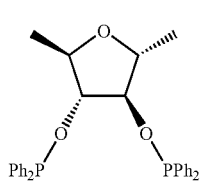
B7

Substrates:

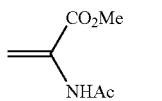
S1

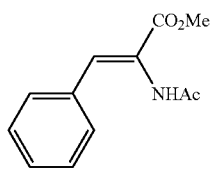
S2

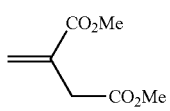
S3

The results of the hydrogenations are compiled in Table 1.

TABLE 1

| Examples | Substrate | Ligand | Solution (ml) | t (min) | Subst/Rh (mol) | % conv. | % ee (R/S) |
|---|---|---|---|---|---|---|---|
| 19 | S1 | B5 | CH$_2$Cl$_2$ 15 | 5 | 100 | 100 | 62(R) |
| 20 | S1 | B5 | CH$_2$Cl$_2$ 15 | 35 | 500 | 93 | 67(R) |
| 21 | S1 | B5 | CH$_2$Cl$_2$ 15 | 10 | 250 | 100 | 65(R) |
| 22 | S1 | B5 | MeOH 15 | 15 | 500 | 63 | 73(R) |
| 23 | S1 | B5 | acetone 15 | 15 | 500 | 99 | 75(R) |
| 24 | S1 | B5 | THF 15 | 15 | 500 | 36 | 63(R) |
| 25 | S1 | B5 | toluene/MeOH 15 | 15 | 500 | 59 | 65(R) |
| 26 | S1 | B6 | CH$_2$Cl$_2$ 15 | 5 | 100 | 95 | 70(R) |
| 27 | S1 | B6 | CH$_2$Cl$_2$/acetone 2:13 | 5 | 100 | 100 | 85(R) |
| 28 | S1 | B6 | CH$_2$Cl$_2$/acetone 2:13 | 5 | 100 | 100 | 87(R) |

TABLE 1-continued

| Examples | Substrate | Ligand | Solution (ml) | t (min) | Subst/Rh (mol) | % conv. | % ee (R/S) |
|---|---|---|---|---|---|---|---|
| 29 | S1 | B6 | CH$_2$Cl$_2$/acetone 2:13 | 15 | 100 | 100 | 90(R) |
| 30 | S1 | B7 | CH$_2$Cl$_2$ 15 | 5 | 100 | 100 | 73(R) |
| 31 | S1 | B7 | CH$_2$Cl$_2$/acetone 2:13 | 5 | 100 | 100 | 79(R) |
| 32 | S2 | B5 | CH$_2$Cl$_2$ 15 | 10 | 100 | 91 | 59(R) |
| 33 | S2 | B5 | Acetone 15 | 10 | 100 | 91 | 73(R) |
| 34 | S2 | B6 | CH$_2$Cl$_2$ 15 | 5 | 100 | 98 | 73(R) |
| 35 | S2 | B6 | CH$_2$Cl$_2$/acetone 2:13 | 5 | 100 | 96 | 80(R) |
| 36 | S2 | B7 | CH$_2$Cl$_2$ 15 | 5 | 100 | 100 | 72(R) |
| 37 | S2 | B7 | CH$_2$Cl$_2$/acetone 2:13 | 5 | 100 | 100 | 75(R) |
| 38 | S3 | B5 | CH$_2$Cl$_2$ 15 | 15 | 100 | 100 | 48(S) |
| 39 | S3 | B5 | acetone 15 | 60 | 100 | 33 | 35(S) |
| 40 | S3 | B6 | CH$_2$Cl$_2$ 15 | 15 | 100 | 96 | 48(S) |
| 41 | S3 | B7 | CH$_2$Cl$_2$ 15 | 5 | 100 | 96 | 53(S) |

Preparation of Phosphine Chlorides:

Examples 42–45

Bis-(2,4-dimethylphenyl)chlorophosphine (B42): A solution of 2.92 ml (2161 mmol) of 4-bromo-1,3-dimethylbenzene in 3 ml of Et$_2$O were added at 0° C. to a suspension of 0.5 g (20.56 mmol) of magnesium turnings in 7 ml of THF and 7 ml of Et$_2$O and also a crystal of iodine. The mixture was heated to room temperature, stirred further overnight and slowly added dropwise at 0° C. to a solution of 1.5 ml (10.31 mmol) of Et$_2$NPCl$_2$ in 8 ml of THF. The mixture was heated to room temperature and the solvent was subsequently removed under reduced pressure. After adding 60 ml of hexane, the mixture was filtered through Celite under argon and admixed with hydrogen chloride for 1 hour. After degassing, the resulting solids were filtered off under argon and dried. Yield: 1.4 g (58.3% of theory). $^1$H NMR (400 MHz, CDCl$_3$) δ, 7.40 (d, Jmeta=4.5 Hz, 2H, arom.), 7.2 (m, 4H, arom.), 2.5 (d, J$_{PH}$=2.0 Hz, 6H, CH$_3$), 2.4 (s, 6H, CH$_3$). $^{31}$P NMR (161.974 MHz, CDCl$_3$) δ, 75.6.

Example 43

Bis-(3,5-dimethylphenyl)chlorophosphine (B43): This product was prepared starting from 5-bromo-1,3-dimethylbenzene in a similar manner to Example 42. Yield: 47.2% of theory. $^1$H NMR (400 MHz, CDCl$_3$) δ, 7.2 (d, 4H, arom.), 7.01 (s, 2H, arom.), 2.37 (s, 12H, CH$_3$). $^{31}$P NMR (161.974 MHz, CDCl$_3$) δ, 83.7.

Example 44

Bis-(4-methoxyphenyl)chlorophosphine (B44): This product was prepared starting from 1-bromo-4-methoxybenzene in a similar manner to Example 42. Yield 45% of theory. $^1$H NMR (400 MHz, CDCl$_3$) δ, 7.48 (t, Jorto=8.4 Hz, J$_{PH}$=8.4 Hz, 4H, arom.), 6.88 (d, Jorto=8.4 Hz, 4H, arom.), 3.75 (s, 6H, CH$_3$O). $^{31}$P NMR (161.974 MHz, CDCl$_3$) δ, 84.2.

Example 45

Bis-(4-trifluoromethylphenyl)chlorophosphine (B45): This product was prepared starting from 1-bromo-4-(trifluoromethyl)benzene in a similar manner to Example 42. Yield 66% of theory. $^1$H NMR (400 MHz, CDCl$_3$) δ, 7.33 (m, 8H, arom.). $^{31}$P NMR (161.9 MHz, CDCl$_3$) δ, 76.3.

Preparation of Aminophosphines:

Example 46

(Diethylamino)-bis(2,4-dimethylphenyl)phosphine (B46): A solution of 2.92 ml (21.61 mmol) of 4-bromo-1,3-dimethylbenzene in 3 ml of Et$_2$O were added at 0° C. to a suspension of 0.5 g (20.56 mmol) of magnesium turnings in 7 ml of THF and 7 ml of Et$_2$O and also a crystal of iodine. The mixture was heated to room temperature, stirred further overnight and slowly added dropwise at 0° C. to a solution of 1.5 ml (10.31 mmol) of Et$_2$NPCl$_2$ in 8 ml of THF. The mixture was heated to 5–10° C., stirred for a further 2 hours and the solvent was subsequently removed under reduced pressure. After adding 60 ml of hexane, the mixture was filtered through Celite under argon and the solvent was subsequently removed under reduced pressure. Yield: 1.37 g (59% of theory). $^1$H NMR (400 MHz, CDCl$_3$) δ, 6.9 (m, 6H), 3.03 (m, 4H, CH$_2$), 2.20 (s, 12H, CH$_3$), 0.81 (t, $^3$J=7.0 Hz, 6H, CH$_3$) $^{31}$P NMR (161.9 MHz, CDCl$_3$) δ, 47.8.

Example 47

(Diethylamino)bis(3,5-dimethylphenyl)phosphine (B47): This product was prepared starting from 5-bromo-1,3-dimethylbenzene in a similar manner to Example 46. Yield 56.8% of theory. $^1$H NMR (400 MHz, CDCl$_3$) δ, 6.90 (d, 4H, arom.), 6.76 (s, 2H, arom.), 2.95 (m, 4H, CH$_2$), 2.11 (s, 12H, CH$_3$), 0.80 (t, $^3$J=7.0 Hz, 6H, CH$_3$). $^{31}$P NMR (161.9 MHz, CDCl$_3$) δ, 61.6.

Example 48

(Diethylamino)bis(4-methoxyphenyl)phosphine (B48): This product was prepared starting from 1-bromo-4-methoxybenzene in a similar manner to Example 46. Yield: 57.2% of theory. $^1$H NMR (400 MHz, CDCl$_3$) δ, 7.48 (dd, Jorto=8.8 Hz, J$_{PH}$=6.4 Hz, 4H, arom.), 6.88 (m, 4H, arom.), 3.81 (s, 6H, CH$_3$O), 3.06 (q, $^3$J=7.2 Hz, 2H, CH$_2$), 0.96 (t, $^3$J=7.2 Hz, 3H, CH$_3$). $^{31}$P NMR (161.9 MHz, CDCl$_3$) δ, 59.5.

Example 49

(Diethylamino)bis(4-trifluoromethylphenyl)phosphine (B49): This product was prepared starting from 1-bromo-4-(trifluoromethyl)benzene in a similar manner to Example 46. Yield: 61.4% of theory. $^1$H NMR (400 MHz, CDCl$_3$) δ, 7.39 (m, 8H, arom.), 2.92 (m, 4H, CH$_2$), 0.82 (t, $^3$J=7.0 Hz, 3H, CH$_3$). $^{31}$P NMR (161.9 MHz, CDCl$_3$) δ, 61.5.

Preparation of Biphosphorus Compounds:

Example 50

2,3-bis-O-(Di(4-methoxyphenyl)phosphino)-1,6-di-O-(tert-butyldiphenylsilyl)-2,5-anhydro-D-mannitol (B50)

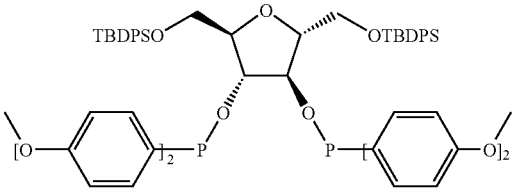

A mixture of 100 mg (0.156 mmol) of 1,6-di-O-(tert-butyidiphenylsilyl-2,5-anhydro-D-mannitol (B2) and 109 mg (0.343 mmol) of diethylaminobis(p-methoxybenzene)phosphine (B48) in 2.2 ml of anhydrous toluene was stirred at 112° C. overnight. After cooling, the solvent was removed under reduced pressure and the crude product was purified by means of column chromatography. Yield: 40 mg (22.7% of theory). $^1$H NMR (400 MHz, C$_6$D$_6$) δ, 7.93 (m, 8H, arom.), 7.67 (m, 8H, arom.), 7.26 (m, 12H, arom.), 6.84 (m, 8H, arom.), 5.38 (dd, J=7.9 Hz, J=4 Hz, 2H, CH), 4.59 (m, 2H, CH), 4.09 (dd, J=10.9 Hz, J=4.2 Hz, 2H, CH$_2$), 3.99 (dd, J=10.9 Hz, J=4.2 Hz, 2H, CH$_2$), 3.37 (s, 6H, CH$_3$O), 3.35 (s, 6H, CH$_3$O), 1.32 (s, 9H, CH$_3$), 1.27 (s, 9H, CH$_3$). $^{31}$P NMR (161.9 MHz, C$_6$D$_6$) δ, 116.3.

Example 51

2,3-bis-O-(Di((4-trifluoromethyl)phenyl)phosphino)-1,6-di-O-(tert-butyidiphenylsilyl)-2,5-anhydro-D-mannitol (B51)

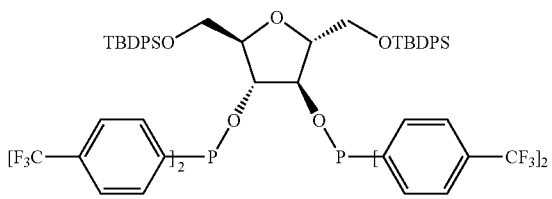

This product was prepared starting from 1,6-di-O-(tert-butyldiphenylsilyl-2,5-anhydro-D-mannitol (B2) and (diethylamino)bis(4-trifluoromethylphenyl)phosphine (B49) in a similar manner to Example 50. Yield: 40 mg (28% of theory). $^1$H NMR (400 MHz, C$_6$D$_6$) δ, 7.9 (m, 2H, arom.), 7.85 (m, 4H, arom.), 7.74 (m, 2H, arom.), 7.40–7.29 (m, 26H, arom.), 7.0 (m, 2H, arom), 5.36 (m, 2H, CH), 4.41 (m, 2H, CH), 4.02 (dd, J=11.4 Hz, J=3.5 Hz, 2H, CH$_2$), 3.79 (dd, J=1.4 Hz, J=3.5 Hz, 2H, CH$_2$), 1.28 (s, 9H, CH$_3$). $^{31}$P NMR δ, (161.9 MHz, C$_6$D$_6$) 111.5.

Example 52

2-O-(Di(2,4-dimethylphenyl)phosphino)-1,6-di-O-(tert-butyidiphenylsilyl)-2,5-anhydro-D-mannitol (B52)

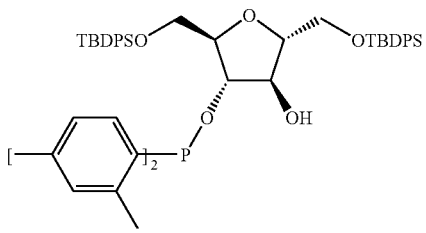

A solution of 337 mg (1.219 mmol) of bis-(2,4-dimethylphenyl)chlorophosphine (B46) in 2 ml of anhydrous THF was added to a solution of 300 mg (0.468 mmol) of 1,6-di-O-(tert-butyldiphenylsilyl)-2,5-anhydro-D-mannitol (B2) and 0.26 ml of anhydrous Et$_3$N (1.86 mmol), and stirred at room temperature overnight. After adding ethyl ether, the mixture was filtered through Celite, solvent removed under reduced pressure and the crude product purified by means of column chromatography. Yield: 180 mg (45% of theory). $^1$H NMR (400 MHz, CDCl$_3$) δ, 7.59–6.87 (m, 26H, arom.), 4.47 (m, 1H, CH), 4.31 (m, 1H, CH), 3.99 (m, 2H, CH), 3.69 (m, 3H, CH$_2$), 3.54 (dd, 1H, CH$_2$), 2.79 (s, OH), 2.30 (s, 3H, CH$_3$), 2.17 (s, 3H, CH$_3$), 2.11 (s, 3H, CH$_3$), 2.06 (s, 3H, CH$_3$), 0.96 (s, 9H, CH$_3$), 0.94 (s, 9H, CH$_3$). $^{13}$C NMR (75.4 MHz, CDCl$_3$) δ, 138.1–127.6 (CH, C, arom.), 86.0 ($^2J_{C-P}$=18 Hz, CH), 84.9 (CH), 83.9 ($^3J_{C-P}$=6.13 Hz, CH), 78.0 ($^2J_{C-P}$=4.5 Hz, CH CH), 64.7 (CH$_2$), 64.1 (CH$_2$), 27.1 (CH$_3$), 27.0 (CH$_3$), 21.4 (C), 20.5 (d, $^3J$=48.4 Hz, CH$_3$), 20.3 (d, $^3J$=48.4 Hz, CH$_3$), 19.6 (s, CH$_3$), 19.5 (s, CH$_3$). $^{31}$P NMR (161.9 MHz, CDCl$_3$) δ, 102.9.

Example 53

2-O-(2,4-dimethylphenylphosphino)-3-O-(diphenylphosphino)-1,6-di-O-(tert-butyldiphenylsilyl)-2,5-anhydro-D-mannitol (B53)

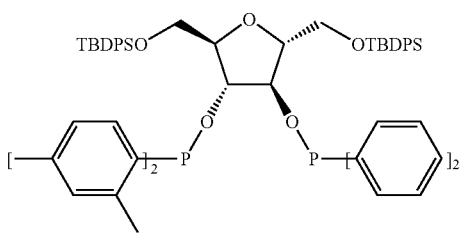

A solution of 0.0125 ml (0.066 mmol) of chlorodiphenylphosphine was added to a solution of 58 mg (0.06 mmol) of 2-O-(2,4-dimethylphenylphosphino)-1,6-dideoxy-2,5-anhydro-D-mannitol (B52) and 0.032 ml (0.23 mmol) of anhydrous Et$_3$N in 0.5 ml of anhydrous THF. The mixture was heated to room temperature and stirred further overnight. After adding degassed, anhydrous hexane, the mixture was filtered through Celite, the solvent removed under reduced pressure and the crude product purified by means of column chromatography. Yield 29.4 mg (45.9% of theory). $^1$H NMR (400 MHz, CDCl$_3$) δ, 7.67–6.91 (m, 36H, arom.), 4.8 (m, 2H, CHx2), 4.15 (m, 2H, CHx2), 3.73 (m, 2H, CH$_2$), 3.59 (m, 2H, CH$_2$), 2.25 (s, 3H, CH$_3$), 2.23 (s, 3H, CH$_3$), 2.19 (s, 3H, CH$_3$), 2.14 (s, 3H, CH$_3$), 1.1 (s, 9H, CH$_3$), 1 (d, 9H, CH$_3$). $^{31}$P NMR (161.9 MHz, C$_6$D$_6$) δ, 114.1, 102.7.

Example 54

2-O-(2,4-Dimethylphenylphosphino)-3-O-(4,8-di-tert-butyl-2,10-dimethyl-12H-dibenzo[δ,γ][1,3,2]dioxaphosphocino)-1,6-di-O-(tert-butyidiphenylsilyl)-2,5-anhydro-D-mannitol (B54)

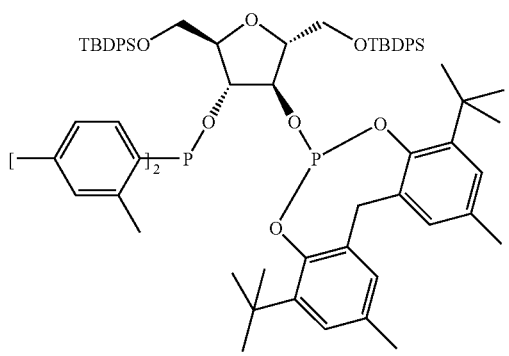

A solution of 100 mg (0.52 mmol) of 4,8-di-tert-butyl-6-chloro-2,10-dimethyl-12h-dibenzo[δ,γ][1,3,2]dioxaphosphocine and 0.100 ml (1.23 mmol) of anhydrous pyridine in 1 ml of anhydrous toluene was added dropwise at 0° C. to a solution of 178 mg (0.202 mmol) of 2-O-(2,4-dimethylphenylphosphino)-1,6-di-O-(tert-butyldiphenylsilyl)-2,5-anhydro-D-mannitol (B52) and 0.100 ml (1.23 mmol) of anhydrous pyridine in 1 ml of anhydrous toluene. The mixture was heated to room temperature and stirred further overnight. After adding degassed, anhydrous hexane, the mixture was filtered through Celite, the solvent removed under reduced pressure and the crude product purified by means of column chromatography. Yield 100 mg (39.6% of theory). $^1$H NMR (400 MHz, C$_6$D$_6$) δ, 7.97–6.38 (m, 30H, arom.), 5.50 (m, 1H, CH), 5.21 (m, 1H, CH), 4.83 (m, 1H, CH), 4.53 (d, J=10.4 Hz, 1H, CH$_2$), 4.50 (m, 3H, CH, CH$_2$), 4.39 (dd, 1H, J=10.8 Hz, J=5.59 Hz, CH$_2$), 4.15 (dd, 1H, J=10.8 Hz, J=5.59 Hz, CH$_2$), 3.3 (d, J=10.4 Hz, 1H, CH$_2$), 2.59 (s, 3H, CH$_3$), 2.51 (s, 3H, CH3), 2.15 (s, 3H, CH$_3$), 2.12 (s, 6H, CH$_3$), 2.1 (s, 3H, CH$_3$), 1.54 (s, 9H, CH$_3$), 1.53 (s, 9H, CH$_3$), 1.36 (s, 9H, CH$_3$), 1.32 (s, 9H, CH$_3$). $^{31}$P NMR (161.9 MHz, C$_6$D$_6$) δ, 128.8, 103.6.

Example 55

2-O-(2,4-Dimethylphenylphosphino)-3-O-(2,10-dimethyl-4,8-bis(1-methylcyclohexyl)-12H-dibenzo[δ,γ][1,3,2]dioxaphosphocino)-1,6-di-O-(tert-butyidiphenylsilyl)-2,5-anhydro-D-mannitol (B55)

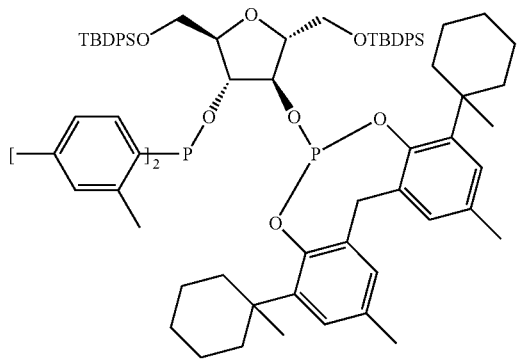

This product was prepared starting from 2-O-(2,4-dimethylphenylphosphino)-1,6-di-O-(tert-butyldiphenylsilyl)-2,5-anhydro-D-mannitol (B52) and 6-chloro-2,10-dimethyl-4,8-bis(1-methylcyclohexyl)-12H-dibenzo[δ,γ][1,3,2]-dioxaphosphocine in a similar manner to Example 54. Yield 71 mg (32.4% of theory). $^1$H NMR (400 MHz, $C_6D_6$) δ, 7.99–6.3 (m, 30H, arom.), 5.44 (m, 1H, CH), 5.14 (m, 1H, CH), 4.81 (m, 1H, CH), 4.57 (dd, J=10.7 Hz, J=4.5 Hz, 1H, $CH_2$), 4.53 (m, 1H, CH, $CH_2$), 4.41 (dd, 1H, J=10.7 Hz, J=4.5 Hz, $CH_2$), 4.29 (dd, 1H, J=10.8 Hz, J=5.0 Hz, $CH_2$), 4.18 (dd, 1H, J=10.8 Hz, J=5.0 Hz, $CH_2$), 3.3 (d, J=12.7 Hz, 1H, $CH_2$), 2.59 (s, 3H, $CH_3$), 2.52 (s, 3H, CH3), 2.24 (s, 3H, $CH_3$), 2.22 (s, 3H, $CH_3$), 2.18 (s, 3H, $CH_3$), 2.17 (s, 3H, $CH_3$), 1.68–1.57 (m, $CH_2$), 1.48 (s, 3H, $CH_3$), 1.47 (s, 3H, $CH_3$), 1.36 (s, 9H, $CH_3$), 1.33 (s, 9H, $CH_3$). $^3$P NMR (161.9 MHz, $CDCl_3$) δ, 128.7, 105.3.

Iridium-catalysed Hydrogenation of Imines and Enamides

Examples 56–78

0.01 Molar equivalent of transition metal compound and 0.012 molar equivalent of ligand were dissolved under argon in degassed $CH_2Cl_2$ (0.015 M) and stirred at room temperature for ½ hour. After adding one molar equivalent of substrate in degassed $CH_2Cl_2$ (0.15 M) under argon, the mixture obtained was hydrogenated in an autoclave at the appropriate temperature under hydrogen pressure. Conversion and ee were determined by chromatography.

Ligands:

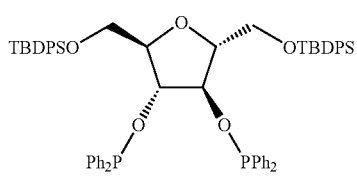

B6

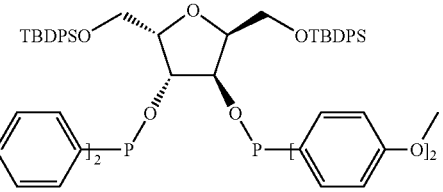

B50

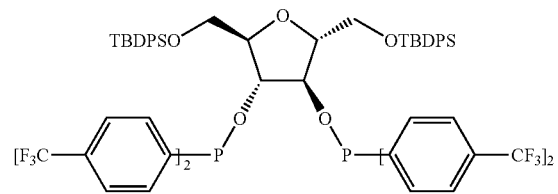

B51

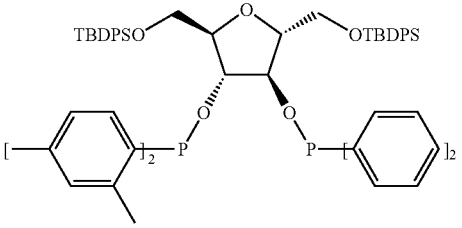

B53

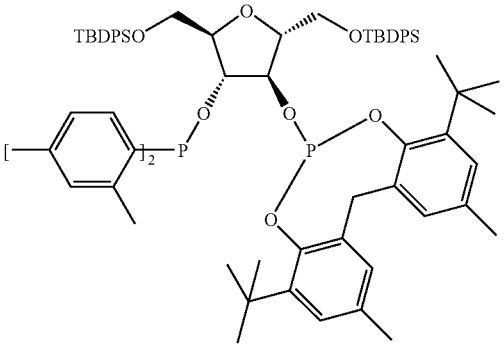

B54

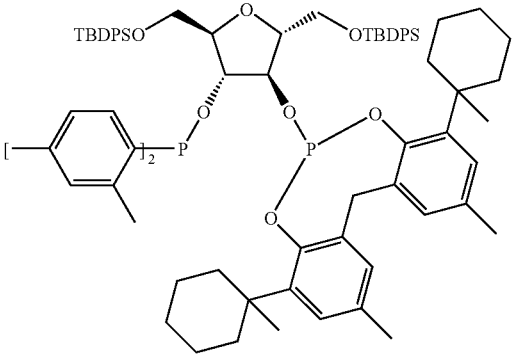

B55

Substrates:

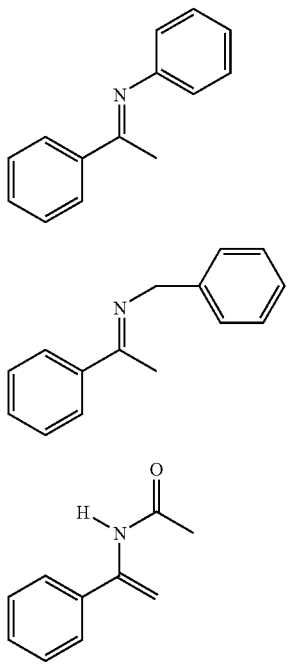

S4

S5

S6

The results of the hydrogenations are compiled in Table 2.

(S4) were dissolved in 10 ml of degassed $CH_2Cl_2$. The mixture was hydrogenated at room temperature and 50 bar of hydrogen pressure. Conversion and ee were determined by gas chromatography. 99% conversion, 67% ee.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A chiral compound of the formula (XIII),

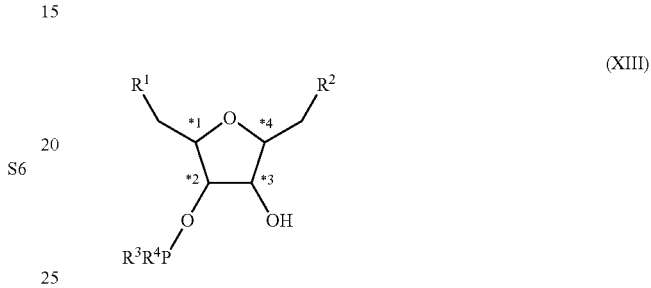

(XIII)

where $R^1$ and $R^2$ may each independently be: hydrogen, $C_1$–$C_{20}$-alkyl, $C_1$–$C_{20}$-fluoroalkyl, $C_2$–$C_{20}$-alkenyl, $C_4$–$C_{24}$-aryl, $C_5$–$C_{25}$-arylalkyl, $C_6$–$C_{26}$-arylalkenyl or $NR^7R^8$, $OR^8$, —($C_1$–$C_8$-alkyl)-$OR^8$, —($C_1$–$C_8$-alkyl)-$NR^7R^8$

TABLE 2

| Examples | Substrates | Ligand | Metal precursor | Additive | T (° C.) | P (bar) | Time (h) | Substrate/metal (mol) | Conversion (%) | ee (%) |
|---|---|---|---|---|---|---|---|---|---|---|
| 56 | S4 | B6 | [Ir(cod)$_2$]BF$_4$ | — | 25 | 70 | 16 | 100 | 100 | 65 |
| 57 | S4 | B51 | [Ir(cod)$_2$]BF$_4$ | — | 25 | 70 | 16 | 100 | 100 | 31 |
| 58 | S4 | B50 | [Ir(cod)$_2$]BF$_4$ | — | 25 | 70 | 16 | 100 | 97 | 71 |
| 59 | S4 | B50 | [Ir(cod)$_2$]BF$_4$ | 4% phthalimide | 25 | 70 | 16 | 100 | 99 | 70 |
| 60 | S4 | B50 | [Ir(cod)$_2$]BF$_4$ | 4% BzNH$_2$ | 25 | 70 | 16 | 100 | 41 | 52 |
| 61 | S5 | B54 | [Ir(cod)$_2$]BF$_4$ | — | 25 | 70 | 16 | 100 | 86 | 73 |
| 62 | S5 | B54 | [Ir(cod)$_2$]BF$_4$ | — | 25 | 70 | 0.5 | 100 | 24 | 68 |
| 63 | S5 | B54 | [Ir(cod)$_2$]BF$_4$ | — | 0 | 70 | 2 | 100 | 4 | 40 |
| 64 | S5 | B54 | [Ir(cod)$_2$]BF$_4$ | 10% I$_2$ | 0 | 70 | 2 | 100 | 1 | 76 |
| 65 | S5 | B54 | [Ir(cod)$_2$]BF$_4$ | — | 50 | 70 | 0.5 | 100 | 80 | 61 |
| 66 | S5 | B54 | [Ir(cod)$_2$]BF$_4$ | 10% phthalimide | 25 | 70 | 16 | 100 | 89 | 75 |
| 67 | S5 | B54 | [Ir(cod)$_2$]BF$_4$ | 10% BzNH$_2$ | 25 | 70 | 16 | 100 | 91 | 75 |
| 68 | S5 | B55 | [Ir(cod)$_2$]BF$_4$ | 10% phthalimide | 25 | 70 | 16 | 100 | 63 | 54 |
| 69 | S5 | B55 | [Ir(cod)$_2$]BF$_4$ | 10% BzNH$_2$ | 25 | 70 | 16 | 100 | 81 | 58 |
| 70 | S6 | B6 | [Rh(nbd)$_2$]PF$_6$ | — | 25 | 3.5 | 24 | 100 | 100 | 48 |
| 71 | S6 | B51 | [Rh(nbd)$_2$]PF$_6$ | — | 25 | 3.5 | 24 | 100 | 99 | 6 |
| 72 | S6 | B50 | [Rh(nbd)$_2$]PF$_6$ | — | 25 | 3.5 | 24 | 100 | 100 | 33 |
| 73 | S6 | B53 | [Rh(nbd)$_2$]PF$_6$ | — | 25 | 3.5 | 24 | 100 | 98 | 20 |
| 74 | S6 | B54 | [Rh(nbd)$_2$]PF$_6$ | — | 25 | 3.5 | 24 | 100 | 97 | 22 |
| 75 | S6 | B6 | [Rh(nbd)$_2$]PF$_6$ | — | 25 | 3.5 | 24 | 100 | 56 | 40 |
| 76 | S6 | B51 | [Rh(nbd)$_2$]PF$_6$ | — | 25 | 3.5 | 24 | 100 | 89 | 50 |
| 77 | S6 | B50 | [Rh(nbd)$_2$]PF$_6$ | — | 25 | 3.5 | 24 | 100 | 89 | 28 |
| 78 | S6 | B54 | [Rh(cod)$_2$]BF$_4$ | — | 25 | 3.5 | 24 | 100 | 98 | 27 |

Example 79

In an autoclave, 28.1 mg (0.022 mmol) of [Ir(cod)(B6)]BF$_4$ (B18) and 0.39 g(2 mmol) N-(phenylethylidene)aniline or —$O_2CR^8$ where $R^7$ and $R^8$ are each independently $C_1$–$C_8$-alkyl, $C_5$–$C_{14}$-arylalkyl or $C_4$–$C_{15}$-aryl, or $R^7$ and $R^8$ together are a cyclic amino radical having a total of 4 to 20 carbon atoms, or $R^1$ and $R^2$ are each independently radicals of the formula (II)

  (II)

where
$R^9$ is absent, or is oxygen or methylene and
$R^{10}$, $R^{11}$ and $R^{12}$ are each independently $C_1$–$C_{12}$-alkyl, $C_5$–$C_{15}$-arylalkyl or $C_4$–$C_{14}$-aryl and
$R^3$, $R^4$, $R^5$ and $R^6$ are each independently $R^{13}$, $OR^{14}$ or $NR^{15}R^{16}$ where $R^{13}$, $R^{14}$, $R^{15}$ and $R^{16}$ are each independently $C_1$–$C_{12}$-alkyl, $C_5$–$C_{15}$-arylalkyl or $C_4$–$C_{14}$-aryl, or $NR^{15}R^{16}$ together is a cyclic amino radical having 4 to 20 carbon atoms, or $R^3$ and $R^4$ and/or $R^5$ and $R^6$ in each case together are —O—$R^{17}$—O— where $R^{17}$ is a radical selected from the group of $C_2$–$C_4$-alkylene, 1,2-phenylene, 1,3-phenylene, 1,2-cyclohexylene, 1,1'-ferrocenylene, 1,2-ferrocenylene, 2,2'-(1,1'-binaphthylene), 2,2'-(1,1')-biphenylene and 1,1'-(diphenyl-2,2'-methylene)-diyl, and the radicals mentioned may optionally be mono- or polysubstituted by radicals selected from the group of fluorine, chlorine, $C_1$–$C_8$-alkoxy and $C_1$–$C_8$-alkyl.

2. Process for preparing a chiral compound of the formula (XV)

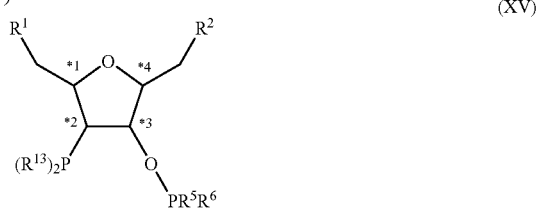  (XV)

where $R^1$, $R^2$, $R^5$, $R^6$ and $R^{13}$ are each as defined in claim 1, comprising,
in step a)
converting chiral compound of the formula (XVI)

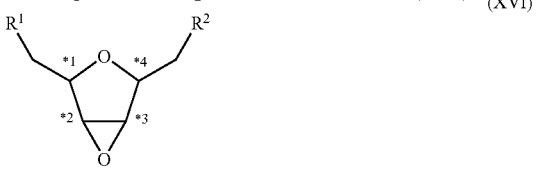  (XVI)

where $R^1$ and $R^2$ are each defined in claim 1, in the presence of compounds of the formula (XVII)

  (XVII)

where
$Met^2$ is lithium, sodium or potassium and
$R^{13}$ is as defined in claim 1,
to a chiral compound of the formula (XVIII)

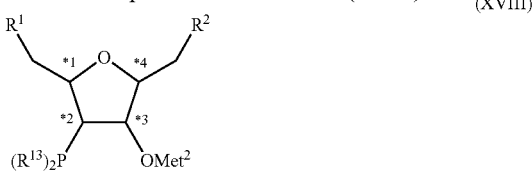  (XVIII)

where $R^1$, $R^2$, $Met^2$ and $R^{13}$ are as defined above,
and, in step b),
reacting the compounds of the formula (XVIII) with compounds of the formula (XIIb)

  (XIIb)

where $R^5$ and $R^6$ are as defined in claim 1 and

Y is chlorine, bromine, iodine, dimethylamino or diethylamino, to give compounds of the formula (XV).

3. Process according to claim 2, characterized in that the compounds of the formula (XVIII) are converted by acidifying to compounds of the formula (XIX)

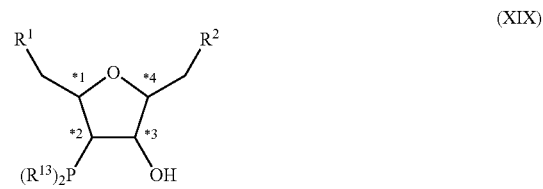  (XIX)

which, in step b), are converted by reacting with compounds of the formula (XIIb) to compounds of the formula (XV).

4. Process according to claim 3, characterized in that step b) is carried out in the presence of a base.

5. A chiral compound of the formula (XVIII)

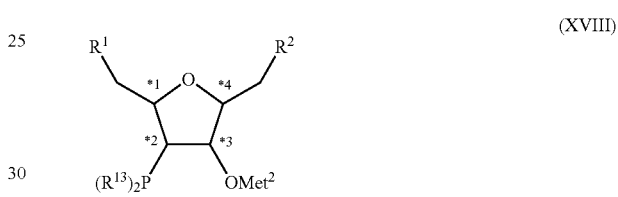  (XVIII)

where $R^1$, $R^2$ and $R^{13}$ are each as defined in claim 1 and $Met^2$ is lithium, sodium or potassium.

6. A chiral compound of the formula (XXIa),

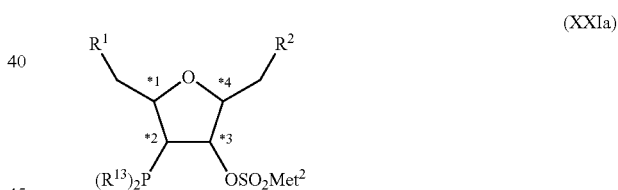  (XXIa)

where $R^1$, $R^2$ and $R^{13}$ are each as defined in claim 1 and $Met^2$ is lithium, sodium or potassium.

7. A chiral Compound of the formula (XXIb),

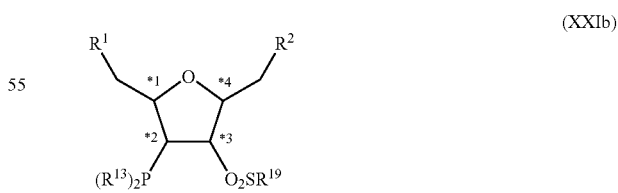  (XXIb)

where $R^1$, $R^2$ and $R^{13}$ are each as defined claim 1, and $R^{19}$ is $C_1$–$C_{12}$-alkyl, $C_1$–$C_{12}$-fluoroalkyl, $C_5$–$C_{25}$-arylalkyl or $C_4$–$C_{24}$-aryl.

* * * * *